(12) United States Patent
Taylor et al.

(10) Patent No.: US 8,153,443 B2
(45) Date of Patent: Apr. 10, 2012

(54) CHARACTERIZATION OF THE CBIR1 ANTIGENIC RESPONSE FOR DIAGNOSIS AND TREATMENT OF CROHN'S DISEASE

(75) Inventors: Kent D. Taylor, Ventura, CA (US); Jerome I. Rotter, Los Angeles, CA (US); Charles O. Elson, Birmingham, AL (US); Stephan R. Targan, Santa Monica, CA (US)

(73) Assignees: Cedars-Sinai Medical Center, Los Angeles, CA (US); The UAB Research Foundation, Birmingham, AL (US)

( * ) Notice: Subject to any disclaimer, the term of this patent is extended or adjusted under 35 U.S.C. 154(b) by 0 days.

(21) Appl. No.: 12/599,549

(22) PCT Filed: May 9, 2008

(86) PCT No.: PCT/US2008/063202
§ 371 (c)(1),
(2), (4) Date: Dec. 18, 2009

(87) PCT Pub. No.: WO2008/141148
PCT Pub. Date: Nov. 20, 2008

(65) Prior Publication Data
US 2010/0284999 A1    Nov. 11, 2010

Related U.S. Application Data

(60) Provisional application No. 60/917,254, filed on May 10, 2007.

(51) Int. Cl.
G01N 33/564 (2006.01)
C12Q 1/68 (2006.01)
A01N 61/00 (2006.01)
A61K 31/00 (2006.01)

(52) U.S. Cl. .................. 436/506; 435/6; 514/1
(58) Field of Classification Search .................. None
See application file for complete search history.

(56) References Cited

U.S. PATENT DOCUMENTS

| 6,858,391 | B2 | 2/2005 | Nunez et al. |
| 2005/0163764 | A1 | 7/2005 | Medzhitov et al. |
| 2006/0003392 | A1 | 1/2006 | Oh et al. |
| 2006/0141478 | A1* | 6/2006 | Brant et al. .................. 435/6 |
| 2006/0154276 | A1 | 7/2006 | Lois et al. |

OTHER PUBLICATIONS

Ogura, Y. et al., A frameshift mutation in NOD2 associated with susceptibility to Crohn's disease, Nature, 2001, vol. 411, pp. 603-606.
Vermeire, S. et al., Current status of genetics research in inflammatory bowel disease, Genes and Immunity, 2005, 6:637-645.

* cited by examiner

*Primary Examiner* — Robert Landsman
(74) *Attorney, Agent, or Firm* — Sean D. Senn; Davis Wright Tremaine LLP

(57) ABSTRACT

This invention provides methods of diagnosing or predicting susceptibility to Crohn's Disease by determining the presence or absence of genetic variants. In one embodiment, the present invention provides methods to diagnose and/or predict susceptibility to Crohn's Disease in an individual by determining the presence or absence of anti-Cbir1 reactivity and the presence or absence of TLR5 risk variants. In another embodiment, the present invention provides methods to diagnose Crohn's Disease by determining the presence or absence of NFKB1 haplotype H3 and/or ASCA expression. In another embodiment, the present invention provides methods of diagnosing Crohn's Disease by determining the presence or absence of Cbir1 specific peripheral blood T cell proliferation.

11 Claims, 17 Drawing Sheets

SEQUENCE LISTING

```
<160> NUMBER OF SEQ ID NOS: 20

<210> SEQ ID NO 1
<211> LENGTH: 278
<212> TYPE: DNA
<213> ORGANISM: Homo sapiens
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t

<400> SEQUENCE: 1
ggcgatgaca aacgtcattt cctcctcccc actgaagtga tctatgattt aaaattttag      60
gcctcccaaa gccacgtgac tttcattagg gcactcttgg gatgcaaaaa ttcttttatt     120
attattatta ttattattat tattattatt atnctttaag ttctagggta catgtgcaca     180
acgcagngnt ttattacata tgtatacatg cgccatgatg gtgtgctgca cccattaact     240
cgtcatttac attaggtata tctcctnatg ctatcctt                             278

<210> SEQ ID NO 2
<211> LENGTH: 876
<212> TYPE: DNA
<213> ORGANISM: Homo sapiens
```

```
<400> SEQUENCE: 2
cctgagcaca tggtcactgt ctttattatg gtgatggtct catgggtata tatatatatc      60
aaaaacaact ctctctctct ctctctctcc aatcccccaa ccccatctct tacaacaaga     120
aagtatgtcc ctagtatatc tggaagccat cttttgacca agagaaaagc cagcatgagg     180
aaactgttaa cacagggaca gaagaaaaga aaatgtctct gaagggaaga gagccagaat     240
tgtgattrca ttaaacctaa agattttcaa cgatgtgacc tgatgaaatt ccataatggt     300
taagtcattt tgagtcataa ttttacatct tttcacctta ggtgaaaagc atcctaacca     360
agataagtat atgctcagca ttatattgat aatttataat acgccattgg aaaaaaactc     420
tcttcctggc atttaattat attacttatt tcaaagaaaa tgcagtaaaa aactgatctg     480
tatatctact gatatgtcta tcagtaaaac agataagtat atctatgtat acctactatg     540
cataagcctt acaggtgcta catagaggtg atatctgtcg gttatactct ttgtcttccc     600
ttctttcttt ttgataacag tgccccaatt tacgcttagc taccataatc tagcattact     660
aattcatgtc ttccagatga gatagaccct ccttgtcact aaaagtagac atgtgactca     720
cagcatttgt agaagatagt aatggaacac aggtcccaaa ttacccctcc aatctcttct     780
cattactttc cccacaagaa aaaagctact gcaagtaagc ggggcatcta agcagggtca     840
cttgaggtcc aggcttcaag gccttttaaaa gaagaa                              876

<210> SEQ ID NO 3
<211> LENGTH: 601
<212> TYPE: DNA
<213> ORGANISM: Homo sapiens

<400> SEQUENCE: 3
catgttcatg gactttgtta agtagaggtt ttcagcatta cagtttatga ataaccata       60 tttaactcaa agatttttttt ataaagctca taatctgaaa aaatgcttat ggtattacta   120
aaacatttaa tagctctggc atcaaaatat tctacatact ggtgatcttt tagtaaatag    180
taaaggttag ggtcaagata ttcaataatt tttttctagc agaatcccac aactgaatat    240
tgtcaagcag tttaaactgc attcgtgttt gttaaaactt taaagggaa acttaaaact     300 raagtatgtt gttttttctga ttttaatatt gtgctttcta gagatgaatc cttttactgt  360
ttgaggcact ataggaatta tgtatttaaa tgtatgtatt taaatttgaa gcaatgtact    420
tttttgagtt tataaacttg ggaagacagg aaataaaaag atttgtttcc tgtagaattt    480
tacattcatg atttaattga attgctaaaa tggaaagaac atgtacgatt aatggagact   540
tggaatctga gattattcat ccatattgat acacctgcaa ttcctaaatg ccctcccctg    600
c                                                                    601

<210> SEQ ID NO 4
<211> LENGTH: 601
<212> TYPE: DNA
<213> ORGANISM: Homo sapiens

<400> SEQUENCE: 4
actagaacaa ataatttatt aaaaagtatc tggcgccttc caaaagggga acatttcatt     60
ctgaaagagg catttatgaa ctagaaaaaa aatgccttttt agtttcaaag ttttagaggc   120
accagagcaa gattataaag taattggaat gataaaaggt gcttgtaaaa ttgaaaaatg    180
taattttttg gtgaagttag aatttctgta cactccattg aaactgtaat atcaaatact    240
aatacctcca aaaagaaaac aatgctacaa gcactgcttg gtaatctaag aattgttaac   300
```

```
rcttatctaa attaatcaac caaaaagtta aaacaaaata tgttattttg ttatgttacc      360
tctagaatta aacacctatc acccataaat ctgtgactgt taaaagttac tagatggcaa      420
acctcaggaa caagcaggca gttagcaggg tttactgtac tttccacttt catactttaa      480
tgatttttcc aacactatag aagctggggc ctcatcctag cacagtttgt tcattatttt      540
tcagttgtag cattttttaa aagttggcct tgaatttctg aattgaacca tttatttttt      600
t                                                                     601

<210> SEQ ID NO 5
<211> LENGTH: 603
<212> TYPE: DNA
<213> ORGANISM: Homo sapiens

<400> SEQUENCE: 5
gctagctagc tatactttct atttcttttt ccatggtgtg aaaatcttcc tagaaacctc       60
actactggga aagagatgc agagattagt cccatcttct cccctggaaa tttactatcg      120
cccttttggc ttcaaggtcc ttcctcaaaa gcaaagaatt gaacaaggga aagtgagggg      180
aagggctggg ggaacaggga ggtagaaggg gttttccctg gtcttttcta atcctttagt      240
tccagacgct tagttggtat ttcaacattt tagaaataaa acctgctttt ataattaatg      300
caaatattac ttagtgattc atccttttcca aatgattctt ggtttctttt gacatttcat      360
ttttaaattg tgaattaaca ttgacatcac catagcgtta ctgttacctc agctctttac      420
agtgaactgt attgcaaagg ctataaaagt tcaattttta actatcaccc acgtgagcct      480
tggactgctg ttaggctttt raaactgtga tcctttggca agaattggtg tataaatcat      540
ggggaggata ttgaagggga agatcatgtt taatttggca gttgggtgcc tgcaattgac      600
aga                                                                   603

<210> SEQ ID NO 6
<211> LENGTH: 808
<212> TYPE: DNA
<213> ORGANISM: Homo sapiens

<400> SEQUENCE: 6
ctatggtggt aaatataccc ctcatctagc tatccaatgt caaggcctga aagaatgcta       60
gagagcacct ctgggactat ttacagaata actgaaaata taactgacag tacaaggagt      120
agacaactaa gcactgagct cactcatttc ttttaccttc agtttcctag cataacacaa      180
aatacctgga atttagtggg tgtgttaagc tgaataacga ccccctaaac atgtctgcat      240
cctaatcctc agaaactgtg agtgctacct tatatgacaa aaggaaattt acgtatgtca      300
ttaaggtaat gataataaga tgaagagagt gtcttgaatt gtccaggtgg gcctgatgag      360
aggggttcag gaaatcacac tgaatagtag gaagtatgac aatggaagca agaggctgga      420
gtgatgagag ggtgcacagg gaaagcaggc agccactaga agctcaaaag gcaaagagat      480
gagagcygca agaaggaaag cagccctgcc aacaccttga ttctagattt ctgagctcct      540
gactcagaag tataaatttg tgttgtttta agccccaagt atgtggtaat gtgttagggc      600
agcaacagag tgggcatgca gaatattttg aagaaagtac attttatctt aataaattac      660
tattcattac ttatcaaaaa acattgtaac cgctggctca tttaggactt taaaactgta      720
tttctgagct tgctatttat tttagcctaa agaagttata tgtttgaaat gtctgtggac      780
agcatggaaa ccagccatat tttactttt                                       808
```

```
<210> SEQ ID NO 7
<211> LENGTH: 601
<212> TYPE: DNA
<213> ORGANISM: Homo sapiens

<400> SEQUENCE: 7
tttcaaattg gttattattt tggaggttgt gctttcatgt tcctaggtat ttctttgttt      60
gactgtgaaa atatttaagt gtgaaaaacc tagagagaga gctttctttt aagtcactaa     120
aatcggattc ttttgatgtt agaaaaaaaa aagactctag attgaaggaa gaagcttaaa     180
ttgatttgaa aaattaaagt gtgctttata tgaacttgtt tcaacatcct cttgaaagac     240
tggcgtgtct cctgttgtat gtcacagttt gttcatcatg tgttgtggaa tacccttcca     300
rttcctgatt gacctaggag agctttgaaa tgcaggctaa ttatcacagt tttagactga     360
ttgatcactt agtgtttctg cagatttatt ccagtagggt tctgtcagtt tgaagtgttt     420
attttctttg gtcttgttta atccctatta taatcatatc ctttagagga aattttagat     480
gaagttttct actagtattt attattataa aacctccagt atggtgtcta taatttggtg     540
tttctgtggt ttgctttagt aatctttcag gattttagaa agaactaatg gttatttaaa     600
t                                                                     601

<210> SEQ ID NO 8
<211> LENGTH: 4926
<212> TYPE: DNA
<213> ORGANISM: Homo sapiens

<400> SEQUENCE: 8
aggccagttc acttaccagt aatcaccaca ctctctctgc tttctggcag tttagagaca      60
tggaattttt ttccaattaa tacatatagc ataccaaac tggtaagcac taggagtaga     120
tatataaata tcaaaataca gaggagaaac aaggccttct tcagtgtctg ttgttcccct     180
ttttgtccat gagttctcat catttagctc ccacttacaa gtgagaacat gcagtatttg     240
tttttctgtt cctgcattag tttgctaagg acagtggcct ctagctccat ccatgttcct     300
gcaaaacata tgatcttatt ctttttatg gctgcatagt attccatggt atatatgtac     360
cacattttct ttatttattt atgttattga tagggaattt aggttgattc catgtctttg     420
ctattgtgga tactgccgca gtgaacatta acatgcatgt gtctttatgg tagaatgatt     480
tatattcctt tgattgtgta cccaacagtg ggattgctgg gtcaaatggt agttctattt     540
ttagctcttt gaaaaatcac cacactgcta caaaatcaat gtgcaaaaat cacaagcatt     600
cctatacacc aataacagac aaacagagag caaaatcatg agtgaactcc cattcacaat     660
tgcttcaaag agaataaaat acctaggaat ccaacttaca ggggatgtga aggacctctt     720
caaggagaac tacaaacccc tgcttaatga aataaaagag gacacaaact aatggaagaa     780
cattccatgc tcatggatag aagaatcaa tatcgtgaaa atggccatac tgcccaaggt     840
aatttataga ttcaatgcca tccccatcaa gctaccaatg acttcttca cagaattgga     900 aaaaactact ttcaagttca tatggaacca aaaagagcc tgcattgcca agacaatcct     960
aagccaaaag aacaaagctg gaggcgtcac actacctgac ttcaaactat actacaaggc    1020
tacagtaacc aaaacagcat ggtactggta ccaaaacaga gatatagacc aatggaacag    1080
aacagagccc tcagaaataa taccgtacat ctacaactat ctgatctttg acaaacctga    1140 caaaacaag aaatggggaa aggattccta tttaataaat ggtgctggga aactggcta    1200 gccatatgta gaaagctgaa actggatccc ttccttacac cttatacaaa aattaattca    1260
agatggatta aagacttaaa tgttatatct aaaaccataa aaaccctaga agaagaccta    1320
```

```
ggcaatacca ttcagcacat gggcatgggc aaagacttca tgactaaaac accaaaagca   1380
atggcaacca aagccaaaat tgacaaatgg gatctaatta aactaaagag cttctccgca   1440
gcaaaagaaa ctaccatcag agtgaacagg caacctacag aatgggagaa aattttttaca  1500 atgtatccat ctgacaaagg gctaatatcc agaatctata agaacttaa ataaatttac    1560 aagaaaaaat caaacaaccc catcaaaaag tgggcaaagg atatgaacag acacttctca   1620
aaagaagaca tttatgcagc caaaagacac atgaaaaaat gctctcatta tcactggcca   1680
tcagagaaat gccaatcaaa accacaatga gataccatct cacaccagtt agaatggcaa   1740
tcattaaaaa gtcgaaacaa caggtgctgg agaggttgtg gagaaatagg aacacttta    1800 cactgttggt gggactgtaa actagttcag ccattgtgga agacagtgtg gcgattcctc   1860
aaggatctag aactagaaat gccatttgac ccagccatcc cattactggg tatataccca   1920
aaggtttata aatcatgctg ctataaagac acatgcacac ttatgtttat tgcagcatta   1980
ttcacaatag caaagacttg gaaccaaccc aaatgtccat cagtgataaa ctggattaag   2040
aaaatgtggc atatacat catggaatac tatgcagcca taagaaagga tgagctcatg     2100
tcctttgtag gacgtgggt gaagctgaa accatcattc tgagcaaact atcgcaagga     2160
cagaaaacca acactgcat gttctcactc ataggtggaa attgaacaat gagaacactt    2220
ggacacaggg tggggaatat cacacccctg ggcctgtggt ggggtggggg gagggatagc   2280
attaggagat atacctaatg taaatgctga gttactgggt gcagcacacc aacatggcac   2340
gtgtatacat atgtaacaaa cctgcacatt gtgcacatgt accctagaac ttaaagtata   2400
ataaaaaata agcaagttta caagggcaaa aataaaacaa aaagaaaaa gcaccacact    2460 gcttccacag tggctgaact aatttgcact cccaccagca gtatataagt gtaccctctt   2520
ctccacagcc gtgccagcat ctgttatctt ttgactttt aataaaagcc attctgacag    2580
gtgtgagatc atatctcatt gtgttttaat ttgcgtttct ctagtgagct ttttccatat   2640
gtttgttggt ggcatgtgtg tcttctcttg aaaagtatct aaaacagtca cttatctttt   2700
aaagaaactt tttaaatcag aaaaaaggtg tttatattta accacgtatt tatcatttgc   2760
agtgctgttc attctgtttc ttaggtcaaa atttctatct ggtatcattt tcttctgcct   2820
caggcacttc ctttattat actgctgatc tgatgctgat taattctttc agtaggtgta    2880
tgttttcata gcttttttatt ttatctttgt ttttcaaaga tattttgaag agtatagaat  2940
tttaggtaga caggccgggc gcagtggctc acgcctgaaa tcccagcact ttggaaggcc   3000
gaggcgggca ggtcacctga ggtcaggagt tcaagaccaa cctgaccaac atggagaaac   3060
cccgtctcta ctaaaaatac aaaattagcc aggcatggtg gtgcatgcct gtaatcccag   3120
ctactcgaga ggccgaggca ggagaatcac ttgaacctgg gaggcagagg ttgcggtgag   3180
ccgagatcgc acaattgcac tccggcctgc gcaacaagaa agaaactccg tctcaaaaaa   3240
aaagaattat aggttgacag tattattctt tcacatcctt aaactatgtt gttccactgt   3300
cttctgattt gccttgtttc caagaagtca cctgtcaatc taatctttgt tcctctgtat   3360 ataattttt tttctctcta gcagcttttc agattttctc ttcctcactc gttttaagca    3420
atttgattat atggatatta gcatagtttc cttcatgttg cttgtgcttg gggttcatcg   3480
agatccttag atctctgggt ttatatattt agtacgtttt aaaactttt ggccattatt    3540 ttttcaaata tattttctgt ccactcctct tcatcttctt ctggaacccc agttgcacat   3600
atatttggct atgtgaaatt tcctacagct cactgatgac ctgttttta aaaaatcttt    3660 tttttctctt tcattttgga aagttttatt actgtgtctg cacgttcacc aatattttg    3720
```

```
tctgtagtgt ctaatatgtt cttaattcca tctagtgtat ttttcctct tagacattgt    3780 aatttgcaat ttctatagat ttgtttgggg tctttttttt tcatatctgc catgttactc    3840
cttaacatac caatgctttc ttcttttct gatcatatgg aatatataat agctattcaa    3900
tgtacttgtg tacaaattct gtcttctgga tctattttg tttagttttt gtcctaatta    3960
tgaattatat ttttctattt ctttccatgc ctgttagttt tttattggat gacaggtatt    4020
ttgaattttg tatcgttaag tcttggattc ctttttttt tttttttttt gatgtgcttt    4080
taaatacgtt tgaggattgg gatgaagtta aatttgggaa cagtttgatt ttttgattc     4140 tttctaaact tacttttaag ctttatcaga gagaccagag aaacctttac tctagggtta    4200
atttgacatc attgctaagg cagtaccttt ctgaattttc aacctgatgc tccatgtatt    4260
acaagatttc ttgaactatt ccagccccat atgtgttaca rtaattttc tgcctccacc     4320 tctgtggtgg ttcttttccc agctttgaca tatttcctca cacacagcac tcagctgaag    4380
actccagtga tctctgagtg tatctctgtt tgcggtttct tcctttccgg tactctgctt    4440
gtgagtttta gcctccttgg cttcctccaa tatttaactg tgtctcctca acctcagaga    4500
ttgccaggct ctgttggggt tcctccttcc tgtgctgcag cctgggactc tttaggcatt    4560
aagccagagt aattacaggg ttcaccttat ttatttccct tttcttaaag attactgttc    4620
tgtgctgcct gttttctagt gtctaaaaac catttcttca tgtatttag atatttaagg     4680 ttcaaaccag tctgtttac tctatcgtta cctgaagcag aagactgact tctgtactgt     4740
ttcatttgtt aaccagagta aatccttcat tattcacata ataattaat aaggatgatg     4800 tttttctcac agggactaga ttaggcaata tacatgaaaa gcatattatt gacagtaaag    4860
tgtaagatgc tacacagatg tttatcattg ctattacaaa ggagataacc ccgttttcct    4920
gcagtt                                                               4926

<210> SEQ ID NO 9
<211> LENGTH: 601
<212> TYPE: DNA
<213> ORGANISM: Homo sapiens

<400> SEQUENCE: 9 taacccccgtt ttcctgcagt tagggaagtt ctatatggga gtaaggctga aagggccaaa    60
agatataggt attgtttctg aaaaactgcc tatgcttcta tgcatataag tatgtcatgt    120
tgcatatttt tctgtgctgt attaattcat gcattccttt atcaacagat acttattaaa    180
cactcatatg tcaggcattg ttctagggac tagagatctc tgccttcaag gagcttattt    240
tctagtggta tattttctgt tctgtgtctt agctatccac ttttttcatc tgcctggaca    300
ygtgacttat tctgtctctg ggcctctggt atgagtgctc atttcattct gccttataac    360
tcctattttc ttcctacttt tatctgacct tcctacctta gcttgttcat tctttccttc    420
aatccagttg tcatgaaatc tctttctttc ctctactaat ttttttttc tttctttctt    480 tctgagtaaa agccagagat ctggccccct gcttacctct ctgaattctt tacttacttc    540
tgacaacttg ctcatttcac tccagctaca ttgacctcct tgcctttgtt gtgttttgaa    600
a                                                                    601

<210> SEQ ID NO 10
<211> LENGTH: 601
<212> TYPE: DNA
<213> ORGANISM: Homo sapiens

<400> SEQUENCE: 10
```

```
cacatgagat tcatacaaa atcccagtgt atggacatgg taggctttga ttaaaatagg      60
ggtgaagggc cctgccagct cggccttccg agaggctgtc ccacctctcc ttacttccct    120
atcaggagct gctggaggtc ttttgaatgc ttctgcctac acaaaatgat gtgaaaatca    180
ctgctttaat ttaaacaccc ttcttaaaa gtagacacag aagaaaaata tggataattt     240
ttttagactt tctgaggaaa aaatagatt tcttctccag aaatatgtct tcaaataatg     300 ycagttttg ctaacacaga gaatcatgaa gaaagaaaac ccaggttacc tgtatgtgta     360
tgaacctaga acattcaaa gctcagcttg gtatctaggc tgcctgtctc cctttcccag     420
tggtatctat gcctcagaaa agtatgttat agtgggggta tattcaggtg attactttaa    480
tgcctcgtta tcatagtagg aactatccaa tgcagggatt agagaatggg gtcacctgaa    540
agttcaaaat tgcacctgta tgcttcatgc acctaccttc caggctgtca ttgatgaaaa    600
g                                                                    601
```

<210> SEQ ID NO 11
<211> LENGTH: 691
<212> TYPE: DNA
<213> ORGANISM: Homo sapiens

<400> SEQUENCE: 11

```
ttcaaaccct gcttaacagt catattcaag gaattactta ttttatgttt ataaatagga    60
tctgcaaagg acacagcaca acaggattag tagctgtgat ttttttttgg agacagagtc   120
tcactctgtc acccagactg gaatgcagtg gcgcgatctc ggctcactgc aacctccacc   180
tcccaggttc aagcgattct tctgcctcag cctcctgagt agctgggatt acaggcgtgc   240
accaccacac ccagctaatt tttgtatttt tagtagagat ggggtttcac catgttggtc   300
tggctggtct tgaactcctg atctcgtaat ctgccagcct cggcctccca agtgctggg    360 attacaggca tgagccactg cgtctggcca gtagctatga tttttttttt atatcctaaa   420
ctctttactg tatcatttgg ttacatatgt tgagactctc cagtgtgtta gagacaaaaa   480
ccctgaaacc rccaccattg atacttctat cccttctgat ttggggactc tcagaagact   540
atacgtccat ttttccccta ccttaccacc agtctgatta tgggcagtg attctggctt    600 ccctagtatg ccttctaggt gtcaaacaca cacccaatgg caactttgat ttgagaatta   660
gaaactgcta agatttgaac tcttgattat c                                   691
```

<210> SEQ ID NO 12
<211> LENGTH: 201
<212> TYPE: DNA
<213> ORGANISM: Homo sapiens

<400> SEQUENCE: 12

```
taaaggttct ctagtaacta ttcttaatgg aaaatgatac agttctctaa ataatttgga    60
ttatttgaca gttaagcatt cttcccaaat acctttcact matctaagta catttctgtg   120
accatctgtc atgatcaaat tcctctcccc acccacccct agaaacaca ctcaaaatag     180 tccaagtgca ccgagttagg a                                              201
```

<210> SEQ ID NO 13
<211> LENGTH: 1810
<212> TYPE: DNA
<213> ORGANISM: Homo sapiens

<400> SEQUENCE: 13

```
ttggctaatt ctgacatttg gctaataaca tcctcacagt atgtcccaag tatcttctgc    60
```

```
ccttccyacc acggtgagca gtcatgacag tgagggtggc ataggtggga tgtgtggctg    120
gcagaagcca gtgggcaaga gttgtccaca gaatagtcca tgagcttttt agagcccggc    180
cattccccca gtgaatttgt gctttctccc ctcagacgag ctccgagaca gtgacagtgt    240
ctgcgacagc ggcgtggaga catccttccg caaactcagc tttaccgagt ctctgaccag    300
tggtgcctca ctgctaactc tcaacaaaat gccccatgat tatgggcagg aaggacctct    360
agaaggcaaa atttagcctg ctgacaattt cccacaccgt gtaaaccaaa gccctaaaat    420
tccactgcgt tgtccacaag acagaagctg aagtgcatcc aaaggtgctc agagagccgg    480
cccgcctgaa tcattctcga tttaactcga gaccttttca acttggcttc ctttcttggt    540
tcataaatga attttagttt ggttcactta cagatagtat ctagcaatca caacactggc    600
tgagcggatg catctgggga tgaggttgct tactaagctt tgccagctgc tgctggatca    660
cagctgcttt ctgttgtcat tgctgttgtc cctctgctac gttcctattg tcattaaagg    720
tatcacggtc gccacctggc attccttctg accacagcat cattttgcat tcaaattaag    780
ggttaagaaa agagatattt taaaatgaga gtcacttgat gtgccatttt aaaaaaaaag    840
gcatattgct ttttctaatg tggttatttc tctgatttgc aaaaaaaaaa aaaaaaaaa     900 tacttgtcaa tatttaaaca tggttacaat cattgctgaa aatggtattt tccccctttt    960
ctgcattttg ctattgtaaa tatgtttttt agatcaaata ctttaaagga aaaaatgttg   1020
gatttataaa tgctattttt tattttactt ttataataaa aggaaaagca aattgatgac   1080
ctcaccttgt ttgatctgtg caaatacttt tctaagatgc ttccttataa tcatgggatc   1140
attccgtata gcctggttat cacattcaca ttgcctatta gagtcaattt tttaatctag   1200
aaatgaacaa ataattatca aaaggaaagt gttttaacct aagatgaaag ctttggattt   1260
gcctaatcct tacccagctc atcttattta gattgtgcca cctcactttc ctccatctca   1320
tgcaatgcta cacctcttca atgtcttctc cacacctctg tgataaagta ttaagatttc   1380
catataccag agggccctgg actaggagcc ttccagcatg aagctttgct gaacaacagg   1440
tgctggagag gatgtggaga acaggaaca cttttacact gttggtggga ctgtaaacta   1500
gttcaaccat tgtggaagtc agtgtggcga ttcctcaggg atctagaact ggaaatacca   1560
tttgacccag ccatcccatt actgggtata tacccaaagg actataaatc atgctgctat   1620
aaagacacat gcacacgtat gtttattgcg gcattattca caatagcaaa gacttggaac   1680
caacccaaat gtccaacaat gatagactgg attaagaaaa tgtggcacat atacaccatg   1740
gaatgctatg cagccataaa aaatgatgag ttcatgtcct tgtagggac  atggatgaaa   1800 ttggaaatca                                                          1810

<210> SEQ ID NO 14
<211> LENGTH: 401
<212> TYPE: DNA
<213> ORGANISM: Homo sapiens

<400> SEQUENCE: 14
ataagattgc agatgaagca ttttacggac ttgacaacct ccaagttctc aatttgtcat     60
ataaccttct gggggaactt tacagttcga atttctatgg actacctaag gtagcctaca   120
ttgatttgca aaagaatcac attgcaataa ttcaagacca acattccaaa ttcctggaaa   180
aattacagac cttggatctc ygagacaatg ctcttacaac cattcatttt attccaagca   240
tacccgtata cttcttgagt ggcaataaac tagtgacttt gccaaagatc aaccttacag   300
cgaacctcat ccacttatca gaaacaggc tagaaaatct agatattctc tactttctcc   360
```

```
tacgggtacc tcatctccag attctcattt taaatcaaaa t                401
```

<210> SEQ ID NO 15
<211> LENGTH: 601
<212> TYPE: DNA
<213> ORGANISM: Homo sapiens

<400> SEQUENCE: 15

```
agctctgttg ggatgttttt gagggacttt ctcatcttca agttctgtat ttgaatcata    60
actatcttaa ttcccttcca ccaggagtat ttagccatct gactgcatta aggggactaa   120
gcctcaactc caacaggctg acagttcttt ctcacaatga tttacctgct aatttagaga   180
tcctggacat atccaggaac cagctcctag ctcctaatcc tgatgtattt gtatcactta   240
gtgtcttgga tataactcat aacaagttca tttgtgaatg tgaacttagc acttttatca   300
rttggcttaa tcacaccaat gtcactatag ctgggcctcc tgcagacata tattgtgtgt   360
accctgactc gttctctggg gtttccctct tctctctttc cacggaaggt tgtgatgaag   420
aggaagtctt aaagtcccta agttctcccc ttttcattgt atgcactgtc actctgactc   480
tgttcctcat gaccatcctc acagtcacaa agttccgggg cttctgtttt atctgttata   540
agacagccca gagactggtg ttcaaggacc atccccaggg cacagaacct gatatgtaca   600
a                                                                  601
```

<210> SEQ ID NO 16
<211> LENGTH: 201
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t

<400> SEQUENCE: 16

```
ttgtgaatgt gaacttagca cttttatcan ttggcttaat cacaccantg tcactatagc    60
tgggcctcct gcagacatat attgtgtgta ccctgactcg ytctctgggg tttccctctt   120
ctctctttcc acggaaggtt gtgatgaaga ggaagtctta aagtccctaa agttctccct   180
tttcnttgta tgcactgtca c                                            201
```

<210> SEQ ID NO 17
<211> LENGTH: 4104
<212> TYPE: DNA
<213> ORGANISM: Homo sapiens

<400> SEQUENCE: 17

```
gtgagagagt gagcgagaca gaaagagaga gaagtgcacc agcgagccgg ggcaggaaga    60
ggaggtttcg ccaccggagc ggcccggcga cgcgctgaca gcttccctg cccttcccgt   120
cggtcgggcc gccagccgcc gcagccctcg gcctgcacgc agccaccggc cccgctcccg   180
gagcccagcg ccgccgaggc cgcagccgcc cggccagtaa ggcggcgccg ccgcccggcc   240
accgcgcgcg ctgcgcttcc ctccgcccgc gctgcggcca tggcgcggcg ctgactggcc   300
tggcccggcc ccgccgcgct cccgctcgcc ccgacccgca ctcgggcccg cccgggctcc   360
```

-continued

```
ggcctgccgc cgcctcttcc ttctccagcc ggcaggcccg cgccgcttag gagggagagc    420
ccacccgcgc caggaggccg aacgcggact cgccacccgg cttcagaatg cagaagatg     480
atccatattt gggaaggcct gaacaaatgt ttcatttgga tccttctttg actcatacaa   540
tatttaatcc agaagtattt caaccacaga tggcactgcc aacagcagat ggcccatacc   600
ttcaaatatt agagcaacct aaacagagag gatttcgttt ccgttatgta tgtgaaggcc   660
catcccatgg tggactacct ggtgcctcta gtgaaaagaa caagaagtct taccctcagg   720
tcaaaatctg caactatgtg ggaccagcaa aggttattgt tcagttggtc acaaatggaa   780
aaaatatcca cctgcatgcc cacagcctgg tgggaaaaca ctgtgaggat gggatctgca   840
ctgtaactgc tggacccaag gacatggtgg tcggcttcgc aaacctgggt atacttcatg   900
tgacaaagaa aaaagtattt gaaacactgg aagcacgaat gacagaggcg tgtataaggg   960
gctataatcc tggactcttg gtgcaccctg accttgccta tttgcaagca gaaggtggag  1020
gggaccggca gctgggagat cgggaaaaag agctaatccg ccaagcagct ctgcagcaga  1080
ccaaggagat ggacctcagc gtggtgcggc tcatgtttac agcttttctt ccggatagca  1140
ctggcagctt cacaaggcgc ctggaacccg tggtatcaga cgccatctat gacagtaaag  1200
cccccaatgc atccaacttg aaaattgtaa gaatggacag gacagctgga tgtgtgactg  1260
gaggggagga aatttatctt ctttgtgaca aagttcagaa agatgacatc cagattcgat  1320
tttatgaaga ggaagaaaat ggtggagtct gggaaggatt tggagatttt tcccccacag  1380
atgttcatag acaatttgcc attgtcttca aaactccaaa gtataaagat attaatatta  1440
caaaaccagc ctctgtgttt gtccagcttc ggaggaaatc tgacttggaa actagtgaac  1500
caaaacctt cctctactat cctgaaatca agataaaga agaagtgcag aggaaacgtc   1560
agaagctcat gcccaatttt tcggatagtt tcggcggtgg tagtggtgcc ggagctggag  1620
gcggaggcat gtttggtagt ggcggtggag gaggggcac tggaagtaca ggtccagggt   1680
atagcttccc acactatgga tttcctactt atggtgggat tactttccat cctggaacta  1740
ctaaatctaa tgctgggatg aagcatgaa ccatggacac tgaatctaaa aaggaccctg   1800
aaggttgtga caaaagtgat gacaaaaaca ctgtaaacct ctttgggaaa gttattgaaa  1860
ccacagagca agatcaggag cccagcgagg ccaccgttgg gaatggtgag gtcactctaa  1920
cgtatgcaac aggaacaaaa gaagagagtg ctggagttca ggataacctc tttctagaga  1980
aggctatgca gcttgcaaag aggcatgcca atgccctttt cgactacgcg gtgacaggag  2040
acgtgaagat gctgctggcc gtccagcgcc atctcactgc tgtgcaggat gagaatgggg  2100
acagtgtctt cacacttagca atcatccacc ttcattctca acttgtgagg gatctactag  2160
aagtcacatc tggtttgatt tctgatgaca ttatcaacat gagaaatgat ctgtaccaga  2220
cgcccttgca cttggcagtg atcactaagc aggaagatgt ggtggaggat ttgctgaggg  2280
ctggggccga cctgagcctt ctggaccgct tgggtaactc tgttttgcac ctagctgcca  2340
aagaaggaca tgataaagtt ctcagtatct tactcaagca caaaaggca gcactacttc   2400
ttgaccaccc caacggggac ggtctgaatg ccattcatct agccatgatg agcaatagcc  2460
tgccatgttt gctgctgctg gtggccgctg gggctgacgt caatgctcag gagcagaagt  2520
ccgggcgcac agcactgcac ctggctgtgg agcacgacaa catctcattg gcaggctgcc  2580
tgctcctgga gggtgatgcc catgtggaca gtactaccta cgatggaacc acaccctgc   2640
atatagcagc tgggagaggg tccaccaggc tggcagctct tctcaaagca gcaggagcag  2700
atcccctggt ggagaacttt gagcctctct atgacctgga tgactcttgg gaaaatgcag  2760
```

```
gagaggatga aggagttgtg cctggaacca cgcctctaga tatggccacc agctggcagg    2820
tatttgacat attaaatggg aaaccatatg agccagagtt tacatctgat gatttactag    2880
cacaaggaga catgaaacag ctggctgaag atgtgaagct gcagctgtat aagttactag    2940
aaattcctga tccagacaaa aactgggcta ctctggcgca gaaattaggt ctggggatac    3000
ttaataatgc cttccggctg agtcctgctc cttccaaaac acttatggac aactatgagg    3060
tctctggggg tacagtcaga gagctggtgg aggccctgag acaaatgggc tacaccgaag    3120
caattgaagt gatccaggca gcctccagcc cagtgaagac cacctctcag gcccactcgc    3180
tgcctctctc gcctgcctcc acaaggcagc aaatagacga gctccgagac agtgacagtg    3240
tctgcgacag cggcgtggag catccttcc gcaaactcag ctttaccgag tctctgacca    3300
gtggtgcctc actgctaact ctcaacaaaa tgccccatga ttatgggcag aaggacctc    3360 tagaaggcaa aatttagcct gctgacaatt cccacaccg tgtaaaccaa agccctaaaa    3420
ttccactgcg ttgtccacaa gacagaagct gaagtgcatc caaggtgct cagagagccg    3480 gcccgcctga atcattctcg atttaactcg agaccttttc aacttggctt cctttcttgg    3540
ttcataaatg aattttagtt tggttcactt acagatagta tctagcaatc acaacactgg    3600
ctgagcggat gcatctgggg atgaggttgc ttactaagct ttgccagctg ctgctggatc    3660
acagctgctt tctgttgtca ttgctgttgt ccctctgcta cgttcctatt gtcattaaag    3720
gtatcacggt cgccacctgg cattccttct gaccacagca tcattttgca ttcaaattaa    3780
gggttaagaa aagagatatt ttaaaatgag agtcacttga tgtgccattt taaaaaaaaa    3840
ggcatattgc tttttctaat gtggttattt ctctgatttg caaaaaaaa aaaaaaaaa    3900 aaatacttgt caatatttaa acatggttac aatcattgct gaaaatggta ttttccccct    3960
tttctgcatt ttgctattgt aaatatgttt tttagatcaa atactttaaa ggaaaaatg    4020 ttggatttat aaatgctatt ttttatttta cttttataat aaaggaaaa gcaaattgat    4080 gacctcaaaa aaaaaaaaaa aaaa                                            4104

<210> SEQ ID NO 18
<211> LENGTH: 4104
<212> TYPE: DNA
<213> ORGANISM: Homo sapiens

<400> SEQUENCE: 18
tttttttttt ttttttttga ggtcatcaat ttgcttttcc ttttattata aaagtaaaat      60
aaaaaatagc atttataaat ccaacatttt ttcctttaaa gtatttgatc taaaaaacat     120
atttacaata gcaaaatgca gaaaagggg aaaataccat tttcagcaat gattgtaacc     180
atgtttaaat attgacaagt attttttttt tttttttttt tttgcaaatc agagaaataa     240
ccacattaga aaaagcaata tgccttttt tttaaaatgg cacatcaagt gactctcatt     300
ttaaaatatc tcttttctta accttaatt tgaatgcaaa atgatgctgt ggtcagaagg     360
aatgccaggt ggcgaccgtg ataccttta tgacaatagg aacgtagcag agggacaaca     420
gcaatgacaa cagaaagcag ctgtgatcca gcagcagctg gcaaagctta gtaagcaacc     480
tcatccccag atgcatccgc tcagccagtg ttgtgattgc tagatactat ctgtaagtga     540
accaaactaa aattcattta tgaaccaaga aaggaagcca agttgaaaag gtctcgagtt     600
aaatcgagaa tgattcaggc gggccggctc tctgagcacc tttggatgca cttcagcttc     660
tgtcttgtgg acaacgcagt ggaatttag ggctttggtt tacacggtgt gggaaattgt     720
cagcaggcta aattttgcct tctagaggtc cttcctgccc ataatcatgg ggcattttgt     780
```

```
tgagagttag cagtgaggca ccactggtca gagactcggt aaagctgagt ttgcggaagg    840
atgtctccac gccgctgtcg cagacactgt cactgtctcg gagctcgtct atttgctgcc    900
ttgtggaggc aggcgagaga ggcagcgagt gggcctgaga ggtggtcttc actgggctgg    960
aggctgcctg gatcacttca attgcttcgg tgtagcccat ttgtctcagg gcctccacca   1020
gctctctgac tgtacccccca gagacctcat agttgtccat aagtgttttg aaggagcag   1080 gactcagccg gaaggcatta ttaagtatcc ccagacctaa tttctgcgcc agagtagccc   1140 agttttttgtc tggatcagga atttctagta acttatacag ctgcagcttc acatcttcag   1200
ccagctgttt catgtctcct tgtgctagta aatcatcaga tgtaaactct ggctcatatg   1260
gtttcccatt taatatgtca aatacctgcc agctggtggc catatctaga ggcgtggttc   1320
caggcacaac tccttcatcc tctcctgcat tttcccaaga gtcatccagg tcatagagag   1380
gctcaaagtt ctccaccagg ggatctgctc ctgctgcttt gagaagagct gccagcctgg   1440
tggaccctct cccagctgct atatgcaggg gtgtggttcc atcgtaggta gtactgtcca   1500
catgggcatc accctccagg agcaggcagc ctgccaatga gatgttgtcg tgctccacag   1560
ccaggtgcag tgctgtgcgc ccggacttct gctcctgagc attgacgtca gcccagcgg   1620 ccaccagcag cagcaaacat ggcaggctat tgctcatcat ggctagatga atggcattca   1680
gaccgtcccc gttggggtgg tcaagaagta gtgctgcctt tttgtgcttg agtaagatac   1740
tgagaacttt atcatgtcct tctttggcag ctaggtgcaa aacagagtta cccaagcggt   1800
ccagaaggct caggtcggcc ccagcccctca gcaaatcctc caccacatct tcctgcttag   1860
tgatcactgc caagtgcaag ggcgtctggt acagatcatt tctcatgttg ataatgtcat   1920
cagaaatcaa accagatgtg acttctagta gatccctcac aagttgagaa tgaaggtgga   1980
tgattgctaa gtgtaagaca ctgtccccat tctcatcctg cacagcagtg agatggcgct   2040
ggacggccag cagcatcttc acgtctcctg tcaccgcgta gtcgaaaagg gcattggcat   2100
gcctctttgc aagctgcata gccttctcta gaaagaggtt atcctgaact ccagcactct   2160 cttctttttgt tcctgttgca tacgttagag tgacctcacc attcccaacg gtggcctcgc   2220
tgggctcctg atcttgctct gtggtttcaa taactttccc aaagaggttt acagtgttt    2280 tgtcatcact tttgtcacaa ccttcagggt ccttttttaga ttcagtgtcc atggttccat   2340
gcttcatccc agcattagat ttagtagttc caggatggaa agtaatccca ccataagtag   2400
gaaatccata gtgtgggaag ctatacccctg gacctgtact tccagtgccc cctcctccac   2460
cgccactacc aaacatgcct ccgcctccag ctccggcacc actaccaccg ccgaaactat   2520
ccgaaaaatt gggcatgagc ttctgacgtt tcctctgcac ttcttcttta tctttgattt   2580
caggatagta gaggaaaggt tttggttcac tagtttccaa gtcagatttc ctccgaagct   2640
ggacaaacac agaggctggt tttgtaatat taatatcttt atactttgga gttttgaaga   2700
caatggcaaa ttgtctatga acatctgtgg gggaaaaatc tccaaatcct tcccagactc   2760
caccattttc ttcctcttca taaaatcgaa tctggatgtc atctttctga actttgtcac   2820
aaagaagata aatttcctcc cctccagtca cacatccagc tgtcctgtcc attcttacaa   2880
ttttcaagtt ggatgcattg ggggctttac tgtcatagat ggcgtctgat accacgggtt   2940
ccaggcgcct tgtgaagctg ccagtgctat ccggaagaaa agctgtaaac atgagccgca   3000
ccacgctgag gtccatctcc ttggtctgct gcagagctgc ttggcggatt agctctttt   3060 cccgatctcc cagctgccgg tcccctccac cttctgcttg caaataggca aggtcagggt   3120
gcaccaagag tccaggatta tagcccctta tacacgcctc tgtcattcgt gcttccagtg   3180
```

| | |
|---|---|
| tttcaaatac ttttttcttt gtcacatgaa gtatacccag gtttgcgaag ccgaccacca | 3240 |
| tgtccttggg tccagcagtt acagtgcaga tcccatcctc acagtgtttt cccaccaggc | 3300 |
| tgtgggcatg caggtggata ttttttccat ttgtgaccaa ctgaacaata acctttgctg | 3360 |
| gtcccacata gttgcagatt ttgacctgag ggtaagactt cttgttcttt tcactagagg | 3420 |
| caccaggtag tccaccatgg gatgggcctt cacatacata acggaaacga aatcctctct | 3480 |
| gtttaggttg ctctaatatt tgaaggtatg ggccatctgc tgttggcagt gccatctgtg | 3540 |
| gttgaaatac ttctggatta aatattgtat gagtcaaaga aggatccaaa tgaaacattt | 3600 |
| gttcaggcct tcccaaatat ggatcatctt ctgccattct gaagccgggt ggcgagtccg | 3660 |
| cgttcggcct cctggcgcgg gtgggctctc cctcctaagc ggcgcgggcc tgccggctgg | 3720 |
| agaaggaaga ggcggcggca ggccggagcc cgggcgggcc cgagtgcggg tcggggcgag | 3780 |
| cgggagcgcg gcggggccgg gccaggccag tcagcgccgc gccatggccg cagcgcgggc | 3840 |
| ggagggaagc gcagggcgcg cggtggccgg gcggcggcgc cgccttactg gccgggcggc | 3900 |
| tgcggcctcg gcggcgctgg gctccgggag cggggccggt ggctgcgtgc aggccgaggg | 3960 |
| ctgcggcggc tggcggcccg accgacggga agggcagggg aagctgtcag cgcgtcgccg | 4020 |
| ggccgctccg gtggcgaaac ctcctcttcc tgccccggct cgctggtgca cttctctctc | 4080 |
| tttctgtctc gctcactctc tcac | 4104 |

<210> SEQ ID NO 19
<211> LENGTH: 3431
<212> TYPE: DNA
<213> ORGANISM: Homo sapiens

<400> SEQUENCE: 19

| | |
|---|---|
| ggttttcagg agcccgagcg agggcgccgc ttttgcgtcc gggaggagcc aaccgtggcg | 60 |
| caggcggcgc ggggaggcgt cccagagtct cactctgccg cccaggctgg actgcagtga | 120 |
| cacaatctcg gctgactgca accactgcct ccagggttca agcgattctc ttgcctcagc | 180 |
| ctcccaagta gctgggatta cagattgatg ttcatgttcc tgacactact acaagattca | 240 |
| tactcctgat gctactgaca acgtggcttc tccacagtca ccaaaccagg gatgctatac | 300 |
| tggacttccc tactctcatc tgctccagcc cctgacctt atagttgccc agcttttcctg | 360 |
| gcaattgact ttgcccatca atacacagga tttagcatcc agggaagatg tcggagcctc | 420 |
| agatgttaat ttctaattg agaatgttgg cgctgtccga acctggagac aggaaaacaa | 480 |
| aaagtccttt ctcctgattc accaaaaaat aaaatactga ctaccatcac tgtgatgaga | 540 |
| ttcctatagt ctcaggaact gaagtcttta acaaccagg gaccctctgc ccctagaata | 600 |
| agaacatact agaagtccct tctgctagga caacgaggat catgggagac cacctggacc | 660 |
| ttctcctagg agtggtgctc atggccggtc ctgtgtttgg aattccttcc tgctcctttg | 720 |
| atggccgaat agccttttat cgtttctgca acctcaccca ggtcccccag gtcctcaaca | 780 |
| ccactgagag gctcctgctg agcttcaact atatcaggac agtcactgct tcatccttcc | 840 |
| cctttctgga acagctgcag ctgctggagc tcggagccta gtataccccc ttgactattg | 900 |
| acaaggaggc cttcagaaac ctgcccaacc ttagaatctt ggacctggga agtagtaaga | 960 |
| tatacttctt gcatccagat gcttttcagg gactgttcca tctgtttgaa cttagactgt | 1020 |
| atttctgtgg tctctctgat gctgtattga aagatggtta tttcagaaat ttaaaggctt | 1080 |
| taactcgctt ggatctatcc aaaaatcaga ttcgtagcct ttaccttcat ccttcatttg | 1140 |
| ggaagttgaa ttccttaaag tccatagatt tttcctccaa ccaaatattc cttgtatgtg | 1200 |

```
aacatgagct cgagcccctc caagggaaaa cgctctcctt ttttagcctc gcagctaata   1260
gcttgtatag cagagtctca gtggactggg gaaaatgtat gaacccattc agaaacatgg   1320
tgctggagat actagatgtt tctggaaatg gctggacagt ggacatcaca ggaaacttta   1380
gcaatgccat cagcaaaagc caggccttct ctttgattct tgcccaccac atcatgggtg   1440
ccgggtttgg cttccataac atcaaagatc ctgaccagaa cacatttgct ggcctggcca   1500
gaagttcagt gagacacctg gatctttcac atgggtttgt cttctccctg aactcacgag   1560
tctttgagac actcaaggat ttgaaggttc tgaaccttgc ctacaacaag ataaataaga   1620
ttgcagatga agcattttac ggacttgaca acctccaagt tctcaatttg tcatataacc   1680
ttctggggga actttacagt tcgaatttct atggactacc taaggtagcc tacattgatt   1740
tgcaaaagaa tcacattgca ataattcaag accaaacatt caaattcctg gaaaaattac   1800
agaccttgga tctccgagac aatgctctta caaccattca ttttattcca agcatacccg   1860
atatcttctt gagtggcaat aaactagtga ctttgccaaa gatcaacctt acagcgaacc   1920
tcatccactt atcagaaaac aggctagaaa atctagatat tctctacttt ctcctacggg   1980
tacctcatct ccagattctc attttaaatc aaaatcgctt ctcctcctgt agtggagatc   2040
aaacccttc agagaatccc agcttagaac agcttttcct tggagaaaat atgttgcaac   2100
ttgcctggga aactgagctc tgttgggatg tttttgaggg actttctcat cttcaagttc   2160
tgtatttgaa tcataactat cttaattccc ttccaccagg agtatttagc catctgactg   2220
cattaagggg actaagcctc aactccaaca ggctgacagt tctttctcac aatgatttac   2280
ctgctaattt agagatcctg gacatatcca ggaaccagct cctagctcct aatcctgatg   2340
tatttgtatc acttagtgtc ttggatataa ctcataacaa gttcatttgt gaatgtgaac   2400
ttagcacttt tatcaattgg cttaatcaca ccaatgtcac tatagctggg cctcctgcag   2460
acatatattg tgtgtaccct gactcgttct ctggggtttc cctcttctct ctttccacgg   2520
aaggttgtga tgaagaggaa gtcttaaagt ccctaaagtt ctccctttc attgtatgca   2580
ctgtcactct gactctgttc ctcatgacca tcctcacagt cacaaagttc cggggcttct   2640
gttttatctg ttataagaca gcccagagac tggtgttcaa ggaccatccc cagggcacag   2700
aacctgatat gtacaaatat gatgcctatt tgtgcttcag cagcaaagac ttcatgggg   2760
tgcagaatgc tttgctcaaa cacctggaca ctcaatacag tgaccaaaac agattcaacc   2820
tgtgctttga agaaagagac tttgtcccag gagaaaaccg cattgccaat atccaggatg   2880
ccatctggaa cagtagaaag atcgtttgtc ttgtgagcag acacttcctt agagatggct   2940
ggtgccttga agccttcagt tatgcccagg gcaggtgctt atctgacctt aacagtgctc   3000
tcatcatggt ggtggttggg tccttgtccc agtaccagtt gatgaaacat caatccatca   3060
gaggctttgt acagaaacag cagtatttga ggtggcctga ggatctccag gatgttggct   3120
ggtttcttca taaactctct caacagatac taaagaaaga aaagaaaag aagaaagaca   3180
ataacattcc gttgcaaact gtagcaacca tctcctaatc aaaggagcaa tttccaactt   3240
atctcaagcc acaaataact cttcactttg tatttgcacc aagttatcat tttggggtcc   3300
tctctggagg tttttttttt ctttttgcta ctatgaaaac aacataaatc tctcaatttt   3360
cgtatcaaca ccatgttctg tctcactaac ctccaaatgg aaaataatag atctagaaaa   3420
ttgcaactgc c                                                       3431

<210> SEQ ID NO 20
<211> LENGTH: 3430
```

```
<212> TYPE: DNA
<213> ORGANISM: Homo sapiens

<400> SEQUENCE: 20
ggcagttgca attttctaga tctattattt tccatttgga ggttagtgag acagaacatg      60
gtgttgatac gaaaattgag agatttatgt tgttttcata gtagcaaaaa gaaaaaaaaa     120
acctccagag aggaccccaa aatgataact tggtgcaaat acaaagtgaa gagttatttg     180
tggcttgaga taagttggaa attgctcctt tgattaggag atggttgcta cagtttgcaa     240
cggaatgtta ttgtctttct tcttttcttt ttctttcttt agtatctgtt gagagagttt     300
atgaagaaac cagccaacat cctggagatc ctcaggccac ctcaaatact gctgtttctg     360
tacaaagcct ctgatggatt gatgtttcat caactggtac tgggacaagg acccaaccac     420
caccatgatg agagcactgt taaggtcaga taagcacctg ccctgggcat aactgaaggc     480
ttcaaggcac cagccatctc taaggaagtg tctgctcaca agacaaacga tctttctact     540
gttccagatg gcatcctgga tattggcaat gcggttttct cctgggacaa agtctctttc     600
ttcaaagcac aggttgaatc tgttttggtc actgtattga gtgtccaggt gtttgagcaa     660
agcattctgc acccatgtga agtctttgct gctgaagcac aaataggcat catatttgta     720
catatcaggt tctgtgccct ggggatggtc cttgaacacc agtctctggg ctgtcttata     780
acagataaaa cagaagcccc ggaactttgt gactgtgagg atggtcatga ggaacagagt     840
cagagtgaca gtgcatacaa tgaaagggaa gaactttagg gactttaaga cttcctcttc     900
atcacaacct tccgtggaaa gagagaagag ggaaacccca gagaacgagt cagggtacac     960
acaatatatg tctgcaggag gcccagctat agtgacattg gtgtgattaa gccaattgat    1020
aaaagtgcta agttcacatt cacaaatgaa cttgttatga gttatatcca agacactaag    1080
tgatacaaat acatcaggat taggagctag gagctggttc ctggatatgt ccaggatctc    1140
taaattagca ggtaaatcat tgtgagaaag aactgtcagc ctgttggagt tgaggcttag    1200
tccccttaat gcagtcagat ggctaaatac tcctggtgga agggaattaa gatagttatg    1260
attcaaatac agaacttgaa gatgagaaag tccctcaaaa acatcccaac agagctcagt    1320
ttcccaggca agttgcaaca tattttctcc aaggaaaagc tgttctaagc tgggattctc    1380 tgaagggggtt tgatctccac tacaggagga gaagcgattt tgatttaaaa tgagaatctg    1440
gagatgaggt acccgtagga gaaagtagag aatatctaga ttttctagcc tgttttctga    1500
taagtggatg aggttcgctg taaggttgat cttttggcaaa gtcactagtt tattgccact    1560
caagaagata tcgggtatgc ttggaataaa atgaatggtt gtaagagcat tgtctcggag    1620
atccaaggtc tgtaattttt ccaggaattt gaatgtttgg tcttgaatta ttgcaatgtg    1680
attcttttgc aaatcaatgt aggctacctt aggtagtcca tagaaattcg aactgtaaag    1740
ttcccccaga aggttatatg acaaattgag aacttggagg ttgtcaagtc cgtaaaatgc    1800
ttcatctgca atcttattta tcttgttgta ggcaaggttc agaaccttca aatccttgag    1860
tgtctcaaag actcgtgagt tcagggagaa gacaaaccca tgtgaaagat ccaggtgtct    1920
cactgaactt ctggccaggc cagcaaatgt gttctggtca ggatctttga tgttatggaa    1980
gccaaacccg gcacccatga tgtggtgggc aagaatcaaa gagaaggcct ggcttttgct    2040
gatggcattg ctaaagtttc ctgtgatgtc cactgtccag ccatttccag aaacatctag    2100
tatctccagc accatgtttc tgaatgggtt catacatttt ccccagtcca ctgagactct    2160
gctatacaag ctattagctg cgaggctaaa aaaggagagc gttttccctt gtaggggctc    2220
gagctcatgt tcacatacaa ggaatatttg gttggaggaa aaatctatgg actttaagga    2280
```

```
attcaacttc ccaaatgaag gatgaaggta aaggctacga atctgatttt tggatagatc    2340
caagcgagtt aaagccttta aatttctgaa ataaccatct ttcaatacag catcagagag    2400
accacagaaa tacagtctaa gttcaaacag atggaacagt ccctgaaaag catctggatg    2460
caagaagtat atcttactac ttcccaggtc caagattcta aggttgggca ggtttctgaa    2520
ggcctccttg tcaatagtca aggggtata ctggctcccg agctccagca gctgcagctg    2580
ttccagaaag gggaaggatg aagcagtgac tgtcctgata tagttgaagc tcagcaggag    2640
cctctcagtg gtgttgagga cctggggac ctgggtgagg ttgcagaaac gataaaaggc    2700
tattcggcca tcaaggagc aggaaggaat tccaaacaca ggaccggcca tgagcaccac    2760
tcctaggaga aggtccaggt ggtctcccat gatcctcgtt gtcctagcag aagggacttc    2820
tagtatgttc ttattctagg ggcagagggt ccctggttgt ttaaagactt cagttcctga    2880
gactatagga atctcatcac agtgatggta gtcagtattt tattttttgg tgaatcagga    2940
gaaaggactt tttgttttcc tgtctccagg ttcggacagc gccaacattc tcaattagaa    3000
aattaacatc tgaggctccg acatcttccc tggatgctaa atcctgtgta ttgatgggca    3060
aagtcaattg ccaggaaagc tgggcaacta taaggtcagg gggctggagc agatgagagt    3120
agggaagtcc agtatagcat ccctggtttg gtgactgtgg agaagccacg ttgtcagtag    3180
catcaggagt atgaatcttg tagtagtgtc aggaacatga acatcaatct gtaatcccag    3240
ctacttggga ggctgaggca agagaatcgc ttgaaccctg gaggcagtgg ttgcagtcag    3300
ccgagattgt gtcactgcag tccagcctgg gcggcagagt gagactctgg gacgcctccc    3360
cgcgccgcct gcgccacggt tggctcctcc cggacgcaaa agcggcgccc tcgctcgggc    3420
tcctgaaaac                                                          3430
```

CHARACTERIZATION OF THE CBIR1 ANTIGENIC RESPONSE FOR DIAGNOSIS AND TREATMENT OF CROHN'S DISEASE

This application is the National Phase of International Application PCT/US08/63202, filed May 9, 2008, which designated the U.S. and that International Application was published under PCT Article 21(2) in English. This application also includes a claim of priority under 35 U.S.C. §119(e) to U.S. provisional patent application No. 60/917,254, filed May 10, 2007.

GOVERNMENT RIGHTS

This invention was made with U.S. Government support on behalf of National Institute of Diabetes and Digestive and Kidney Diseases (NIDDK) grant P01DK46763. The U.S. Government may have certain rights in this invention.

FIELD OF THE INVENTION

The invention relates generally to the fields of inflammation and autoimmunity and autoimmune disease and, more specifically, to genetic methods for diagnosing and treating Crohn's Disease.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Crohn's disease (CD) and ulcerative colitis (UC), the two common forms of idiopathic inflammatory bowel disease (IBD), are chronic, relapsing inflammatory disorders of the gastrointestinal tract. Each has a peak age of onset in the second to fourth decades of life and prevalences in European ancestry populations that average approximately 100-150 per 100,000 (D. K. Podolsky, N Engl J Med 347, 417 (2002); E. V. Loftus, Jr., Gastroenterology 126, 1504 (2004)). Although the precise etiology of IBD remains to be elucidated, a widely accepted hypothesis is that ubiquitous, commensal intestinal bacteria trigger an inappropriate, overactive, and ongoing mucosal immune response that mediates intestinal tissue damage in genetically susceptible individuals (D. K. Podolsky, N Engl J Med 347, 417 (2002)). Genetic factors play an important role in IBD pathogenesis, as evidenced by the increased rates of IBD in Ashkenazi Jews, familial aggregation of IBD, and increased concordance for IBD in monozygotic compared to dizygotic twin pairs (S. Vermeire, P. Rutgeerts, Genes Immun 6, 637 (2005)). Moreover, genetic analyses have linked IBD to specific genetic variants, especially CARD15 variants on chromosome 16q12 and the IBD5 haplotype (spanning the organic cation transporters, SLC22A4 and SLC22A5, and other genes) on chromosome 5q31 (S. Vermeire, P. Rutgeerts, Genes Immun 6, 637 (2005); J. P. Hugot et al., Nature 411, 599 (2001); Y. Ogura et al., Nature 411, 603 (2001); J. D. Rioux et al., Nat Genet 29, 223 (2001); V. D. Peltekova et al., Nat Genet 36, 471 (2004)). CD and UC are thought to be related disorders that share some genetic susceptibility loci but differ at others.

The replicated associations between CD and variants in CARD15 and the IBD5 haplotype do not fully explain the genetic risk for CD. Thus, there is need in the art to determine other genes, allelic variants and/or haplotypes that may assist in explaining the genetic risk, diagnosing, and/or predicting susceptibility for or protection against inflammatory bowel disease including but not limited to CD and/or UC.

SUMMARY OF THE INVENTION

Various embodiments provide methods of diagnosing susceptibility to Crohn's Disease in an individual, comprising determining the presence or absence of one or more risk variants at the NFkB locus and diagnosing susceptibility to Crohn's Disease based upon the presence of one or more risk variants at the NFkB locus. In another embodiment, the individual is human. In another embodiment, one of the one or more risk variants at the NFkB locus comprises ATA2A03. In another embodiment, one of the one or more risk variants at the NFkB locus comprises SEQ. ID. NO.: 1. In another embodiment, one of the one or more risk variants at the NFkB locus comprises SEQ. ID. NO.: 2, SEQ. ID. NO.: 3, SEQ. ID. NO.: 4, SEQ. ID. NO.: 5, SEQ. ID. NO.: 6, SEQ. ID. NO.: 7, SEQ. ID. NO.: 8, SEQ. ID. NO.: 9, SEQ. ID. NO.: 10, SEQ. ID. NO.: 11, SEQ. ID. NO.: 12 and SEQ. ID. NO.: 13.

In other embodiments, the invention provides methods of diagnosing Crohn's Disease in an individual, comprising determining the presence or absence of NFkB haplotype H3, determining the presence or absence of ASCA reactivity, and diagnosing Crohn's Disease based upon the presence of NFkB haplotype H3 and the presence of ASCA reactivity. In other embodiments, the NFkB haplotype H3 comprises SEQ. ID. NO.: 2, SEQ. ID. NO.: 3, SEQ. ID. NO.: 4, SEQ. ID. NO.: 5, SEQ. ID. NO.: 6, SEQ. ID. NO.: 7, SEQ. ID. NO.: 8, SEQ. ID. NO.: 9, SEQ. ID. NO.: 10, SEQ. ID. NO.: 11, SEQ. ID. NO.: 12 and SEQ. ID. NO.: 13.

Other embodiments provide methods of diagnosing Crohn's Disease in an individual, comprising determining the presence or absence of NFkB haplotype H1, determining the presence or absence of Cbir1 reactivity, and diagnosing Crohn's Disease based upon the presence of NFkB haplotype H1 and the presence of Cbir1 reactivity. In other embodiments, the NFkB haplotype H1 comprises SEQ. ID. NO.: 2, SEQ. ID. NO.: 3, SEQ. ID. NO.: 4, SEQ. ID. NO.: 5, SEQ. ID. NO.: 6, SEQ. ID. NO.: 7, SEQ. ID. NO.: 8, SEQ. ID. NO.: 9, SEQ. ID. NO.: 10, SEQ. ID. NO.: 11, SEQ. ID. NO.: 12 and SEQ. ID. NO.: 13.

Other embodiments provide methods of treating Crohn's Disease in an individual, comprising determining the presence or absence of NFkB haplotype H3, determining the presence or absence of ASCA reactivity, and treating the Crohn's Disease.

Other embodiments provide methods of treating Crohn's Disease in an individual, comprising determining the presence or absence of NFkB haplotype H1, determining the presence or absence of Cbir1 reactivity, and treating the Crohn's Disease.

Various embodiments provide methods of diagnosing susceptibility to Crohn's Disease in an individual, comprising determining the presence or absence of one or more risk variants at the TLR5 locus, and diagnosing susceptibility to Crohn's Disease based upon the presence of one or more risk variants at the TLR5 locus. In another embodiment, one of the one or more risk variants at the TLR5 locus comprises SEQ. ID. NO.: 15, SEQ. ID. NO.: 16 and/or SEQ. ID. NO.: 17.

Other embodiments provide methods of diagnosing a Crohn's Disease subtype in an individual, comprising determining the presence or absence of F616L F allele, determining the presence or absence of N592S S allele, determining the presence or absence of OmpC reactivity, and diagnosing the Crohn's Disease subtype based upon the presence of OmpC reactivity and the presence of the F616L F allele or the N592S S allele. In another embodiment, the F616L F allele comprises SEQ. ID. NO.: 16. In another embodiment, the N592S S allele comprises SEQ. ID. NO.: 15. In another embodiment, the individual is Jewish.

Various embodiments also provide methods of diagnosing a Crohn's Disease subtype in an individual, comprising determining the presence or absence of N592S N allele, determining the presence or absence of Cbir1 reactivity, and diagnosing the Crohn's Disease subtype based upon the presence of Cbir1 reactivity and the presence of the N592S N allele. In another embodiment, the N592S N allele comprises SEQ. ID. NO.: 15. In another embodiment, the Crohn's Disease subtype comprises internal penetrating phenotype, perianal perforating phenotype and/or severe fibrostenosis phenotype.

Other embodiments provide methods of treating Crohn's Disease in an individual, comprising determining the presence of a high IL-6 production relative to healthy individuals, and administering a therapeutically effective amount of anti-Cbir1.

Other embodiments provide methods of diagnosing Crohn's Disease in an individual, comprising determining the presence or absence of a high amount of Cbir1-specific IFN-gamma producing cells relative to healthy individuals, and diagnosing Crohn's Disease based upon the presence of a high amount of Cbir1-specific IFN-gamma producing cells relative to healthy individuals.

Other embodiments provide methods of diagnosing Crohn's Disease in an individual, comprising determining the presence or absence of a high amount of Cbir1-specific peripheral blood T cell proliferation relative to healthy individuals, and diagnosing Crohn's Disease based upon the presence of a high amount of Cbir1-specific peripheral blood T cell proliferation relative to healthy individuals.

Other features and advantages of the invention will become apparent from the following detailed description, taken in conjunction with the accompanying drawing, which illustrate, by way of example, various embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

"SNP" as used herein means single nucleotide polymorphism.

"Haplotype" as used herein refers to a set of single nucleotide polymorphisms (SNPs) on a gene or chromatid that are statistically associated.

"Risk variant" as used herein refers to an allele whose presence is associated with an increase in susceptibility to an inflammatory bowel disease, including but not limited to Crohn's Disease and ulcerative colitis, relative to an individual who does not have the risk variant.

"Protective variant" as used herein refers to an allele whose presence is associated with a low probability relative to a healthy individual of developing inflammatory bowel disease. A protective variant is more frequently present in healthy individuals compared to individuals diagnosed with inflammatory bowel disease.

"Risk haplotype" as used herein refers to a haplotype whose presence is associated with an increase in susceptibility to an inflammatory bowel disease, relative to an individual who does not have the risk haplotype.

"Protective haplotype" as used herein refers to a haplotype whose presence is associated with a low probability relative to a healthy individual of developing inflammatory bowel disease. A protective haplotype is more frequently present in healthy individuals compared to individuals diagnosed with inflammatory bowel disease.

As used herein, the term "NFkB" or "NF-kappaB" means Nuclear Factor-kappa B.

As used herein, an example of marker ATA2A03 is provided as SEQ. ID. NO.: 1.

Figure 5:
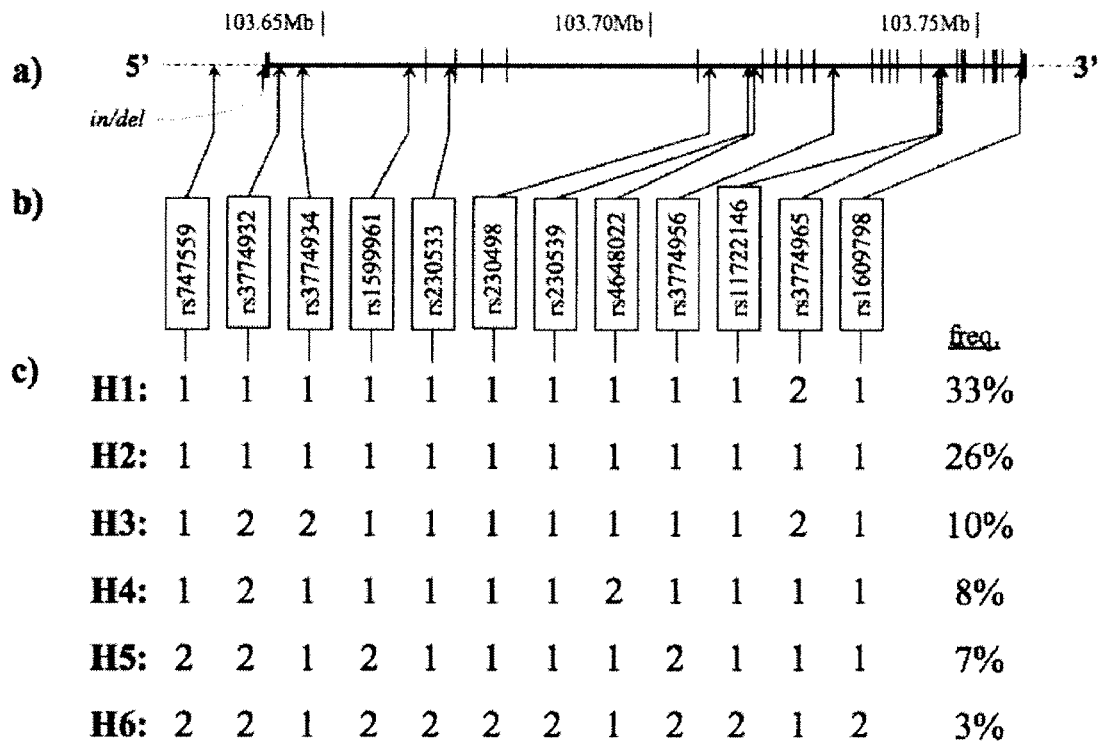
FIGS. 5A-D depict NFKB1 SNPs and haplotypes. This cartoon showing the location of NFKB1 SNPs studied was created with the aid of the UCSC Genome Browser. (a) Diagram of the NFKB1 gene. The NFKB1 gene is located on chromosome 4 at the basepair location shown on Build 16 of the human genome project. Vertical lines show the position of exons. The position of the promoter insertion/deletion polymorphism is also shown. (b) List of SNPs studied. Accession numbers ("rs numbers") in the dbSNP of the National Center for Biotechnology Information are listed along with arrows showing their position along the NFKB1 gene. Polymorphisms genotyped in this study are listed with their positions along the gene. SNPs were selected using the Tagger option of the Haploview program applied to data for the Caucasian population from the International HapMap Project, with some redundancy in case of the failure of an individual SNP in the Illumina genotyping platform. (c) The most common NFKB1 haplotypes observed in this study. The SNP combinations that make up the six major haplotypes are shown, along with the frequency in the controls of this study are listed. "2" refers to the observed minor allele of each SNP in the controls. (d) Haploview analysis. Result of Haploview analysis of the linkage disequilibrium (LD) between the SNPs genotyped in this study.
Figure 6:
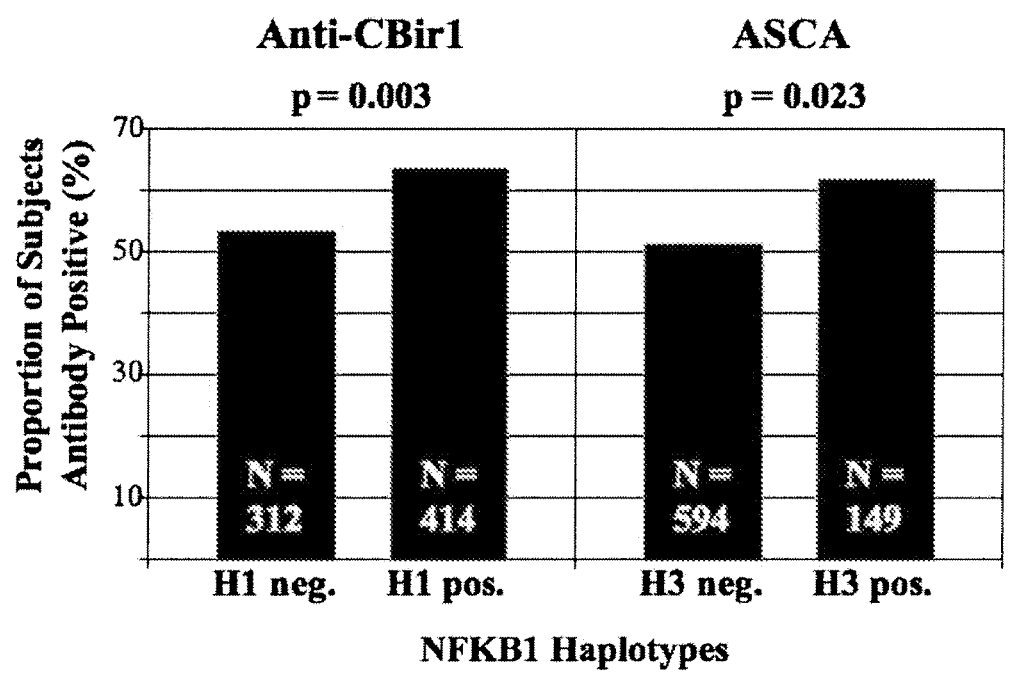
FIG. 6 depicts association of anti-CBir1 expression with NFKB1 haplotypes. Haplotypes of NFKB1 were assigned and tested for association with the presence or absence of antibody expression by chi-square test. P-values are empirical p-values by permutation test in order to correct for multiple comparisons.
Figure 7A:
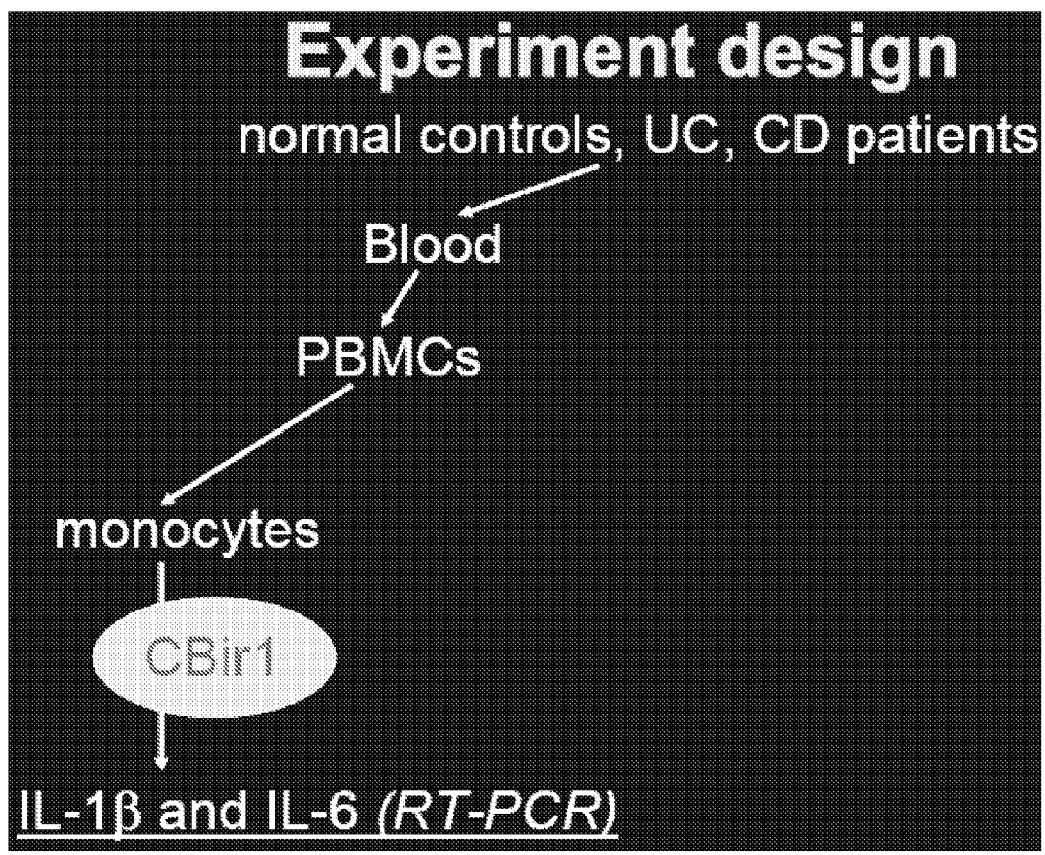
FIGS. 7A-D depict IL-6 and IL-1Beta production among Crohn's disease, ulcerative colitis, control cohort. (a) depicts the experiment design to generate results 7(b)-(d). (b) depicts increased Cbir1 generated IL-6 production in Crohn's disease. (c) depicts the inverse correlation of IL-6 level and magnitude of anti-Cbir1 response in Crohn's disease. (d) depicts the lack of difference in Cbir1 mediated IL-1Beta production among Crohn's disease, ulcerative colitis, and controls.
Figure 7B:
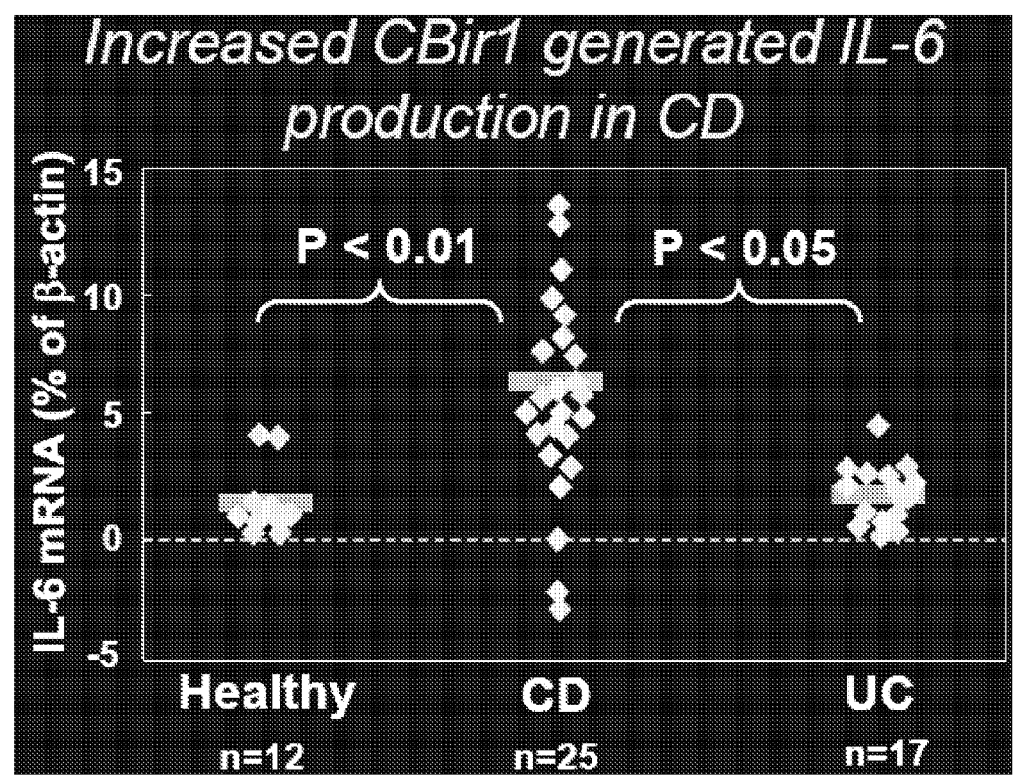
Figure 7C:
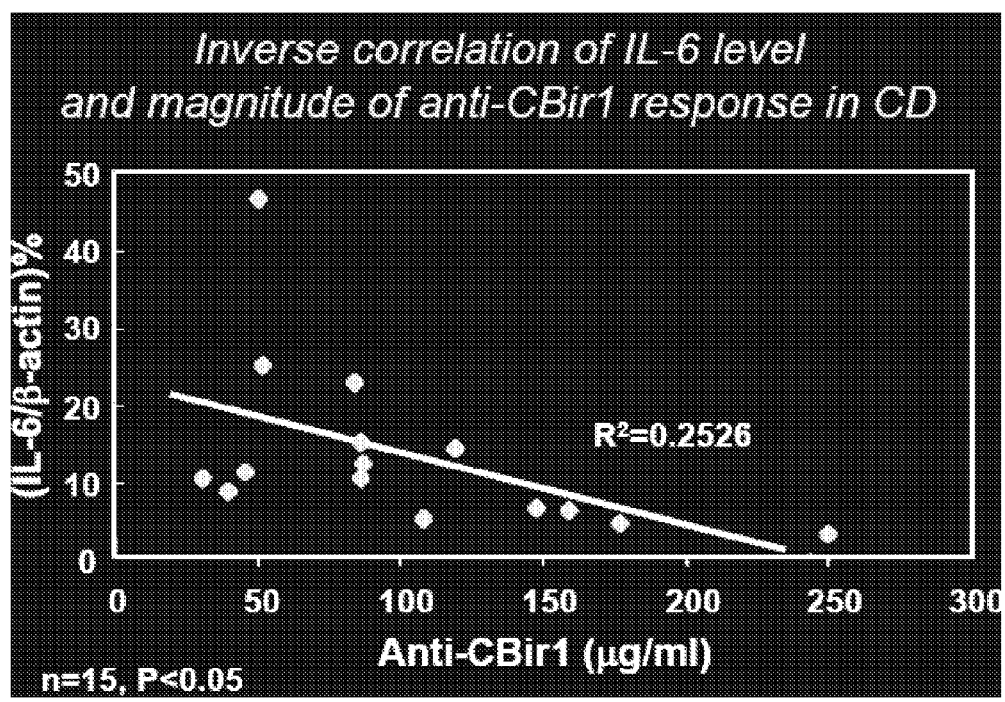
Figure 7D:
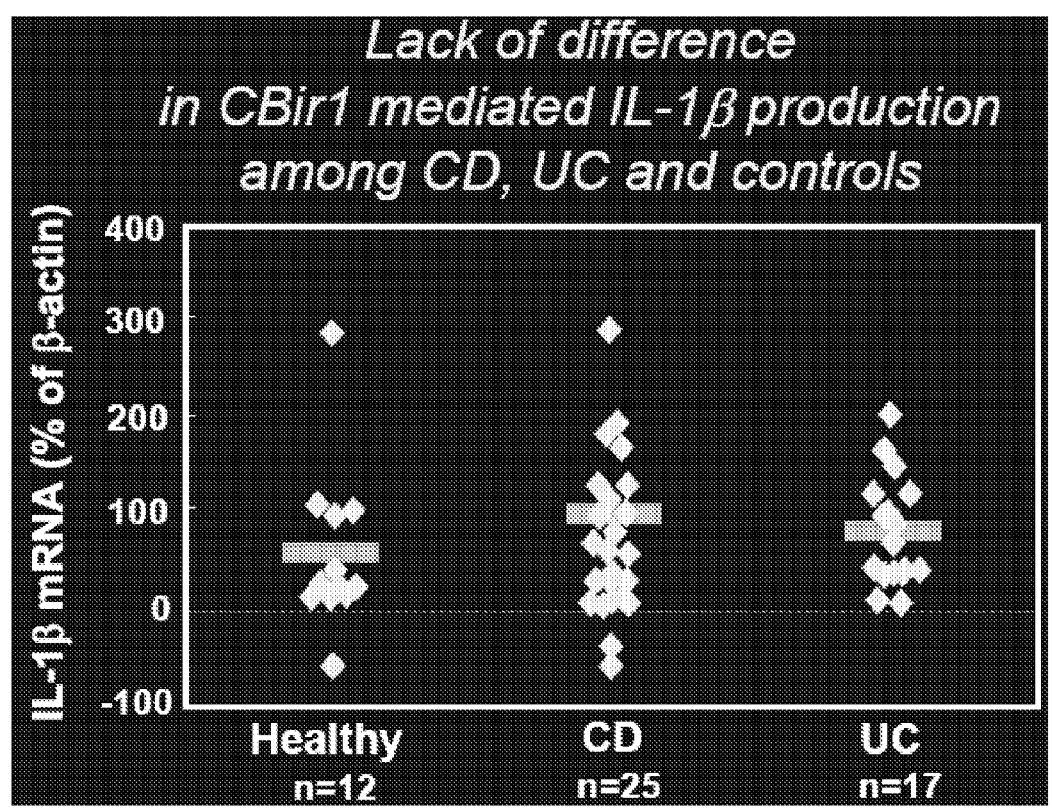
Figure 8A:
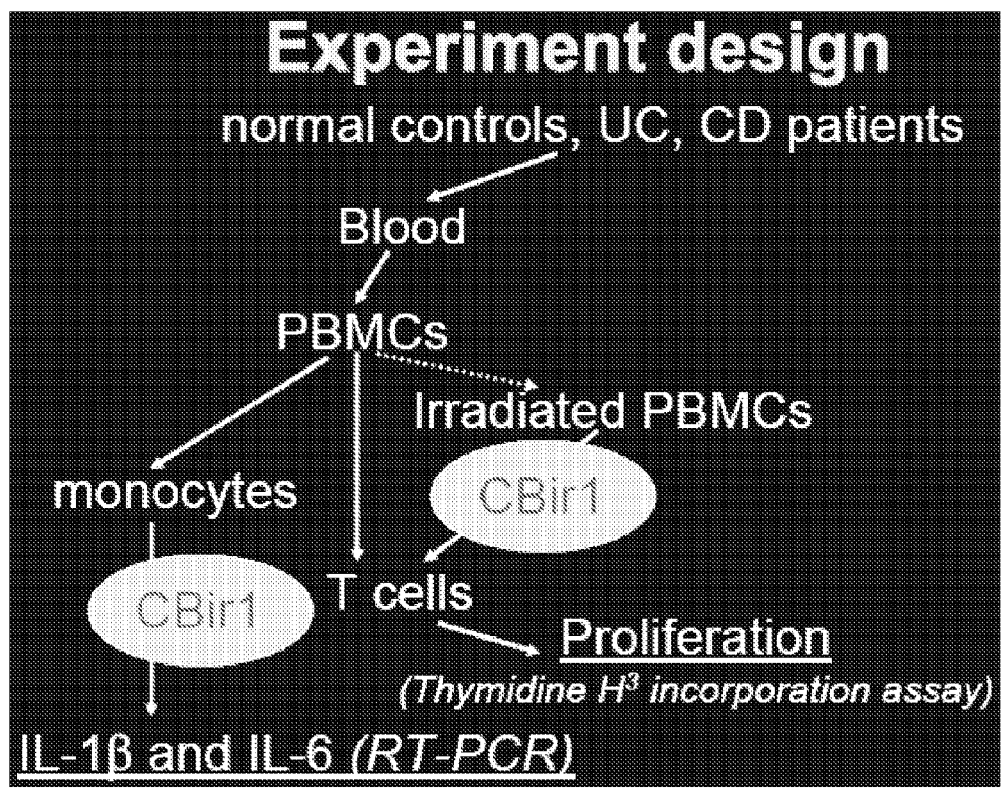
FIGS. 8A-C depict enhanced Cbir1 specific peripheral blood T cell proliferation in Crohn's Disease. (a) depicts the experimental design to generate results 8(b)-(c). (b) depicts enhanced Cbir1 specific peripheral blood T cell proliferation in Crohn's disease. (c) depicts enhanced Cbir1 specific peripheral blood T cell proliferation in Crohn's disease, but not in ulcerative colitis and healthy controls.
Figure 8B:
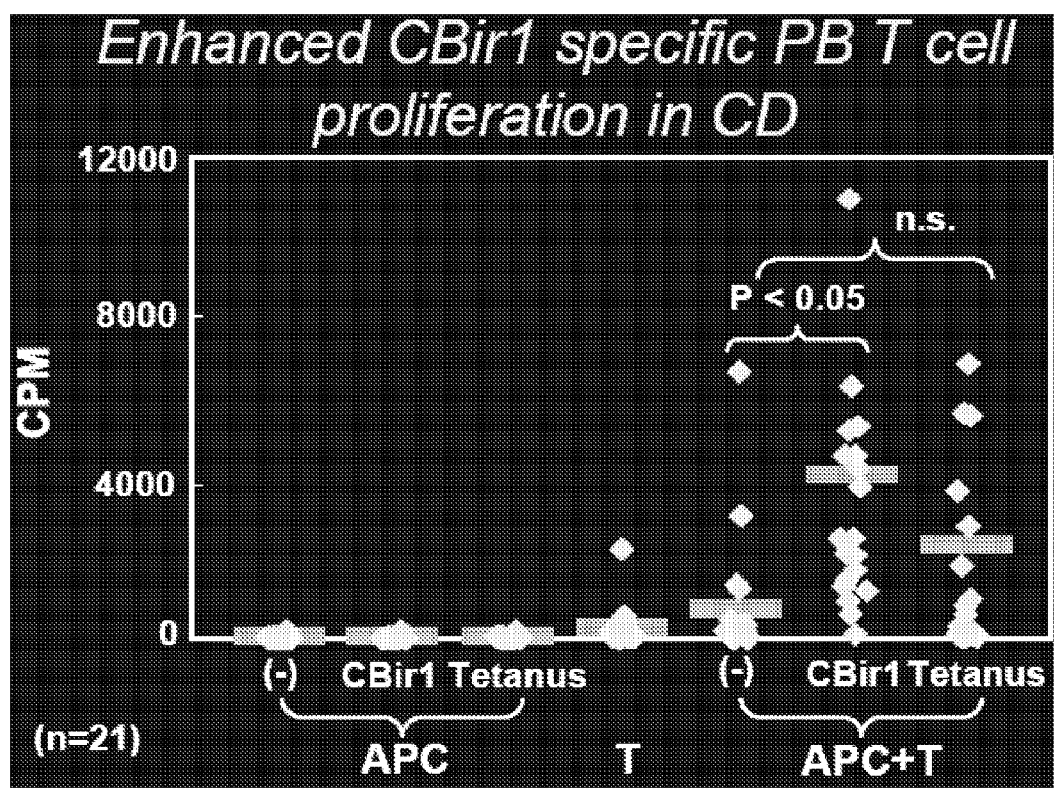
Figure 8C:
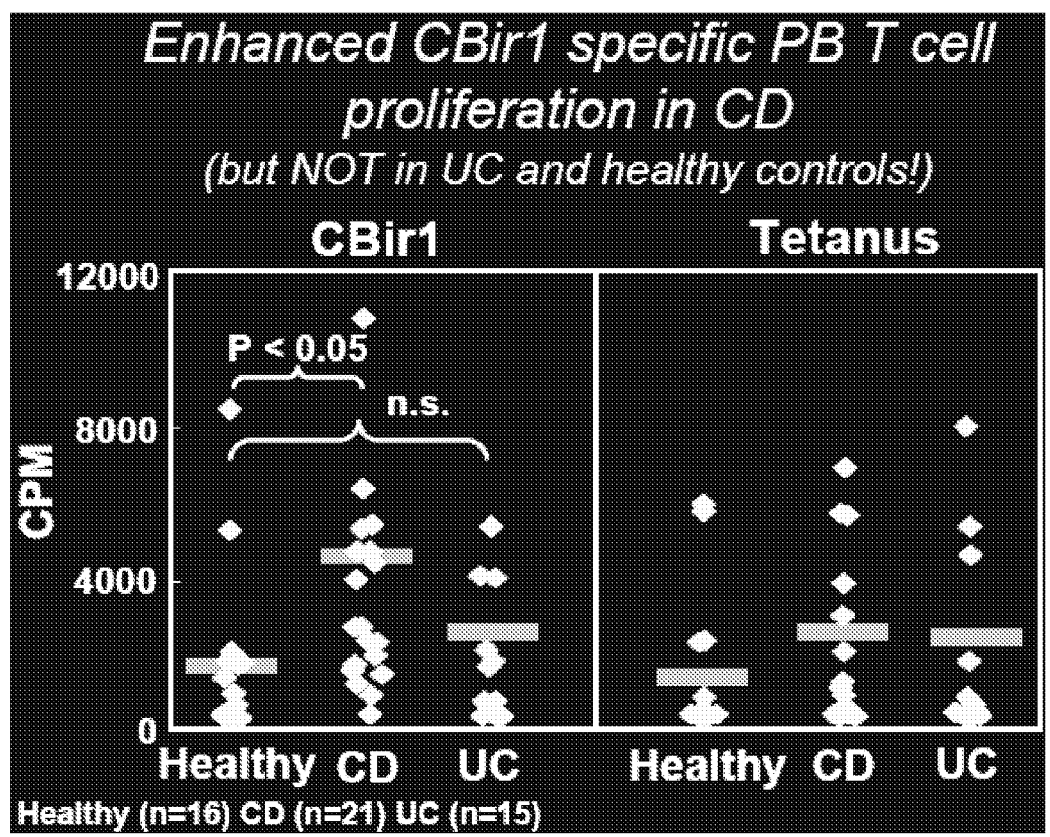
Figure 9A:
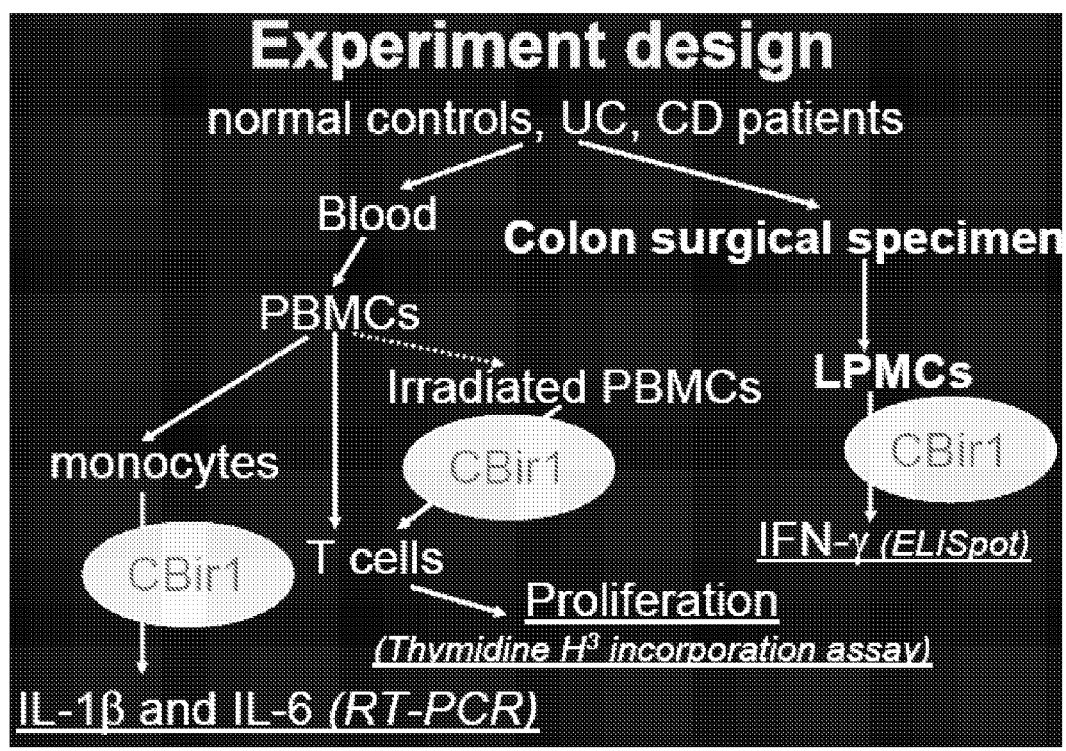
FIGS. 9A-C depict an increased amount of Cbir1 specific IFN-gamma-producing cells from involved Crohn's disease colon compared to ulcerative colitis and control. (a) depicts the experimental design. (b) depicts an example of an IFN-gamma ELISpot assay with lamina propria mononuclear cells from a Crohn's disease patient. (c) depicts increased Cbir1 specific IFN-gamma-producing cells in lamina propria mononuclear cells from involved Crohn's Disease colon.
Figure 9B:
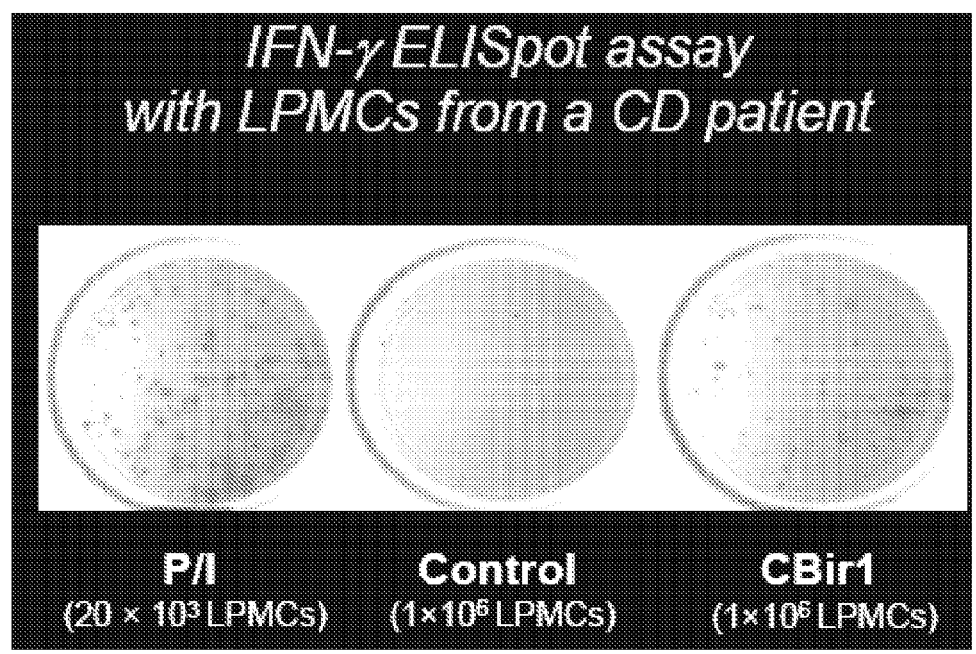
Figure 9C:
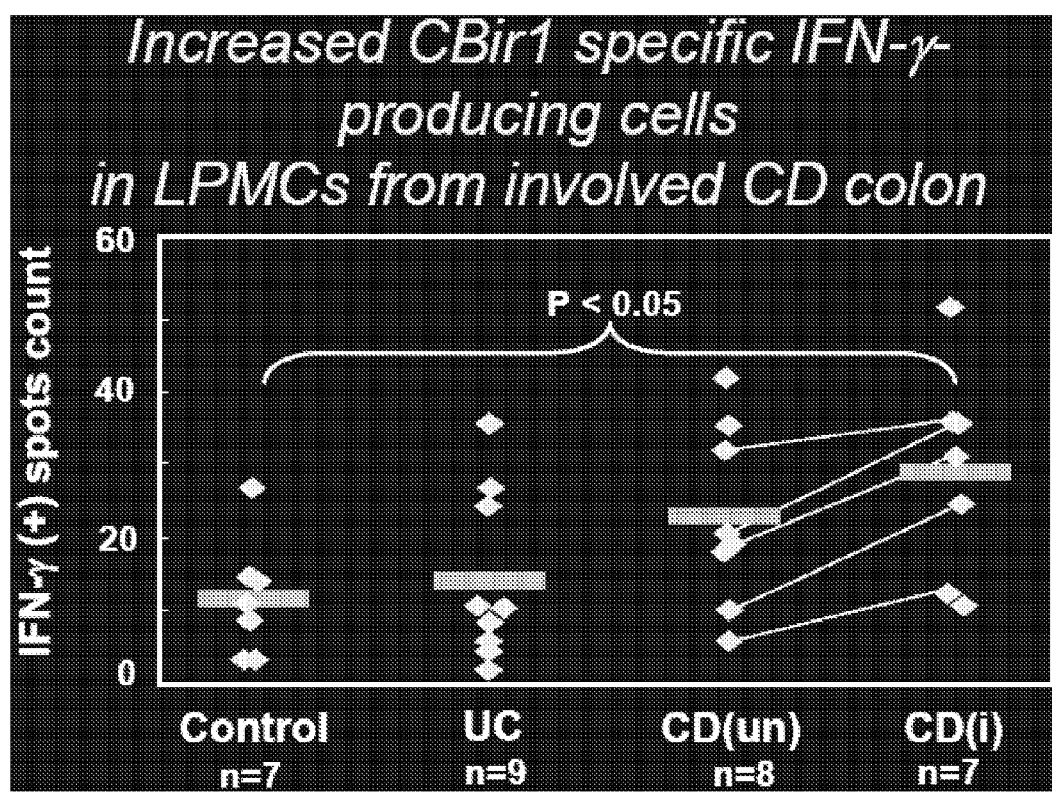

As used herein, NFkB SNPs rs747559, rs3774932, rs3774934, rs1599961, rs230533, rs230498, rs230539, rs4648022, rs3774956, rs11722146, rs3774965, and rs1609798, are described herein as SEQ. ID. NO.: 2, SEQ. ID. NO.: 3, SEQ. ID. NO.: 4, SEQ. ID. NO.: 5, SEQ. ID. NO.: 6, SEQ. ID. NO.: 7, SEQ. ID. NO.: 8, SEQ. ID. NO.: 9, SEQ. ID. NO.: 10, SEQ. ID. NO.: 11, SEQ. ID. NO.: 12 and SEQ. ID. NO.: 13, respectively. The NFkB SNPs and corresponding NFkB haplotypes are also described in FIG. 5. Examples of the NFkB genetic sequence are provided herein as SEQ. ID. NO.: 17 and SEQ. ID. NO.: 18.

As used herein, TLR5 SNPs R392X (rs5744168), N592S (rs2072493) and F616L (rs5744174) are also described herein as SEQ. ID. NO.: 14, SEQ. ID. NO.: 15 and SEQ. ID NO.: 16, respectively. Examples of the TLR5 genetic sequence are provided herein as SEQ. ID. NO.: 19 and SEQ. ID. NO.: 20.

As used herein, the term "biological sample" means any biological material from which nucleic acid molecules can be prepared. As non-limiting examples, the term material encompasses whole blood, plasma, saliva, cheek swab, or other bodily fluid or tissue that contains nucleic acid.

The inventors performed a genome-wide association study testing autosomal single nucleotide polymorphisms (SNPs) on the Illumina HumanHap300 Genotyping BeadChip. Based on these studies, the inventors found single nucleotide polymorphisms (SNPs) and haplotypes that are associated with increased or decreased risk for inflammatory bowel disease, including but not limited to CD. These SNPs and haplotypes are suitable for genetic testing to identify at risk individuals and those with increased risk for complications associated with serum expression of Anti-*Saccharomyces cerevisiae* antibody, and antibodies to I2, OmpC, and Cbir. The detection of protective and risk SNPs and/or haplotypes may be used to identify at risk individuals, predict disease course and suggest the right therapy for individual patients. Additionally, the inventors have found both protective and risk allelic variants for Crohn's Disease and Ulcerative Colitis.

Based on these findings, embodiments of the present invention provide for methods of diagnosing and/or predicting susceptibility for or protection against inflammatory bowel disease including but not limited to Crohn's Disease. Other embodiments provide for methods of treating inflammatory bowel disease including but not limited to Crohn's Disease.

The methods may include the steps of obtaining a biological sample containing nucleic acid from the individual and determining the presence or absence of a SNP and/or a haplotype in the biological sample. The methods may further include correlating the presence or absence of the SNP and/or the haplotype to a genetic risk, a susceptibility for inflammatory bowel disease including but not limited to Crohn's Disease, as described herein. The methods may also further include recording whether a genetic risk, susceptibility for inflammatory bowel disease including but not limited to Crohn's Disease exists in the individual. The methods may also further include a prognosis of inflammatory bowel disease based upon the presence or absence of the SNP and/or haplotype. The methods may also further include a treatment of inflammatory bowel disease based upon the presence or absence of the SNP and/or haplotype.

In one embodiment, a method of the invention is practiced with whole blood, which can be obtained readily by non-invasive means and used to prepare genomic DNA, for example, for enzymatic amplification or automated sequencing.

In another embodiment, a method of the invention is practiced with tissue obtained from an individual such as tissue obtained during surgery or biopsy procedures.

I. Cbir1 and NFkB Variants

As disclosed herein, the inventors investigated the genetic determinants of Cbir1 response in human CD by linkage analysis of Cbir1 expression as a quantitative trait (QTL). The inventors measured Cbir1 serum levels in 968 individuals in 80 CD-only (no UC affected) and 57 Mixed (both CD and UC affected) families was performed by ELISA and a 10 cM genome scan was performed with microsatellite markers. QTL analysis was performed using the SOLAR program. The heritability of expression of serum antibodies to Cbir1 antigen in this study was 0.19 (p=0.0005). A peak multipoint LOD score for Cbir1 expression was observed for human chromosome 4 at 91 cM (LOD=1.82, marker ATA2A03). This LOD increased with bivariate linkage analysis of expression of both ASCA and Cbir1 antibodies (LOD=1.99). This region is syntenic to the mouse chromosome 3 Cdcs1 region containing the Nfkb1 gene.

As further disclosed herein, this observation supports the role of genetic variation that determines response to Cbir1 flagellin in this region in both mouse and human and that genetic variation in the NF-kappa-B gene creates an abnormal innate response to enteric bacterial antigens that results in severe CD.

In one embodiment, the present invention provides a method of diagnosing and/or predicting susceptibility to Crohn's Disease in an individual by determining the presence or absence of marker ATA2A03 and/or anti-Cbir1 reactivity, where the presence of the marker ATA2A03 and/or anti-Cbir1 reactivity is indicative of susceptibility to Crohn's Disease. In another embodiment, the present invention provides a method of diagnosing an individual with Crohn's Disease by determining the presence or absence of the marker ATA2A03 and/or anti-Cbir1 reactivity, where the presence of the marker ATA2A03 and/or anti-Cbir1 reactivity is indicative of Crohn's Disease. In another embodiment, the present invention provides methods of treating Crohn's Disease, comprising determining the presence of marker ATA2A03 and/or anti-Cbir1 reactivity and treating the Crohn's Disease.

As disclosed herein, the inventors determined whether the human NFkB1 gene is associated with anti-Cbir1 expression and tested the relationship between NFkB1 genetic variants and NFkB expression. Single-nucleotide polymorphisms (SNPs) were selected to tag common Caucasian haplotypes and genotyped in 763 Crohn's disease (CD) and 254 controls using Illumina technology. Anti-Cbir1 antibody and *Saccharomyces cerevisiae* antibody (ASCA) were measured by ELISA. Nuclear proteins from Epstein-Barr virus (EBV)-transformed lymphoblastoid cell lines from subjects with specific haplotypes were extracted and electro mobility shift assay (EMSA) was performed. Quantitation of EMSA was performed by electric densitometry.

As further disclosed herein, one NFKB1 haplotype, H3, was associated with ASCA expression (62% of ASCA positive patients had H3 compared with 51% of ASCA negative patients, p=0.023) and another, H1, was associated with anti-Cbir1 expression (64% of anti-Cbir1 positive subjects had H1 compared with 53% of anti-Cbir1 negative subjects, p=0.003). Using EBV-transformed cell lines from H3 positive H1 negative (n=11) and H1 positive H3 negative (n=14) subjects, the median NF-kB expression was lower for patients with H1 compared with patients with H3 (median NF-kB expression for H3 was 1.79 compared with H1, 1.28, p=0.02, Wilcoxon test).

As further disclosed herein, human NFKB1 haplotypes were differentially associated with both ASCA and anti-Cbir1 expression. The anti-Cbir1-associated haplotype (H1) showed less NF-kB induction, even following EBV-signaling, normally a strong inducer. Differences due to H1 may be greater under less strong induction, eg. signals due to TLR in monocytes. These observations in humans are consistent with the reduced induction of NFKB1 driven inflammatory genes that is associated with the colitigenic Cdcs1 locus in the mouse.

In one embodiment, the present invention provides methods to diagnose and/or predict susceptibility to Crohn's Disease in an individual by determining the presence or absence of NF-kappa-B genetic variation and/or anti-Cbir1 reactivity. In another embodiment, the present invention provides methods of treatment of Crohn's Disease in an individual by determining the presence or absence of NF-kappa-B genetic variation and/or anti-Cbir1 reactivity, and treating the Crohn's Disease.

In one embodiment, the present invention provides methods to diagnose and/or predict susceptibility to IBD by determining the presence or absence of NFKB1 haplotype H3 and/or ASCA expression. In another embodiment, the present invention provides methods of treatment of IBD by determining the presence or absence of NFKB1 haplotype H3 and/or ASCA expression, and treating the Crohn's Disease.

In one embodiment, the present invention provides methods to diagnose a Crohn's Disease subtype by determining the presence or absence of NFKB1 haplotype H1 and/or CBir1 expression. In another embodiment, the present invention provides methods of treatment of a Crohn's Disease subtype by determining the presence or absence of NFKB1 haplotype H1 and/or Cbir1 expression, and treating the Crohn's Disease.

In one embodiment, the present invention provides methods to diagnose a Crohn's Disease subtype by determining the presence or absence of NFKB1 haplotype H3 and/or ASCA. In another embodiment, the present invention provides methods of treatment of a Crohn's Disease subtype by determining the presence or absence of NFKB1 haplotype H3 and/or Cbir1 expression, and treating the Crohn's Disease.

In one embodiment, the present invention provides methods to vaccinate an individual in need thereof against Inflammatory Bowel Disease, by administering a composition that includes Cbir1 and/or Ab-Cbir1. In another embodiment, the presence of Cbir1 modulates innate immunity in the individual.

II. TLR5 Polymorphisms are Associated with OmpC and CbiR1 Expression and with Severity of Crohn's Disease in Ashkenazi Jews As disclosed herein, the inventors investigated the association of TLR5 SNPs and serum expression of antibodies to microbial antigens in CD using a case/control design. In 889 CD patients and 236 controls, serum expression of OmpC and Cbir1 was measured by ELISA, and 3 TLR5 SNPs (R392X, N592S, F616L) were genotyped by TaqMan MGB. The TLR5 SNPs R392X, N592S and F616L may by referenced from NCBI by rs5744168, rs2072493 and rs5744174, respectively. Chi-square was used to test for the association of allele with disease, clinical characteristics, and antibody combinations, and Wilcoxon and logistic regression for antibody expression levels and disease severity.

As further disclosed herein, the F616L F allele was associated with the presence of OmpC expression in Jewish cases (the F allele was present in 93.3% of OmpC+, Jewish, CD cases and in 81.2% OmpC−, p=0.0025; p=0.0005 for trend through 3 genotypes). By multivariate analysis, the F/F genotype contributed to a higher level of OmpC expression in both ethnic groups (presence of F/F p=0.019; OR of F/F versus L/L, 2.02 95% CI 1.15-3.58). Similarly, the N592S S allele was associated with the presence of OmpC expression in Jewish cases (30.8% of OmpC+, Jewish, CD cases had the S allele compared with 19.5% OmpC−, p=0.02). In contrast, the N allele was associated with higher levels of Cbir1 flagellin expression (278 for N/N and N/S genotype and 190 for S/S, p=0.05 with logistic regression). On multivariate analysis, the N/N allele was associated with CD severity as defined by internal penetrating, perianal perforating and severe fibrostenosis combined (OR 6.88, 95% CI 1.65-28.6, p=0.0059).

As further disclosed herein, TLR5 SNPs are associated with the level of OmpC expression, particularly in Jews. The observation that the opposite allele of one of the TLR5 SNPs is associated with Cbir1 flagellin, a TLR5 ligand, supports the concept that specific variation in genes of innate immune pathways govern variations between individuals in expression of specific antibodies to microbial antigens. The combination of these immune signals then leads to increasing severity of disease.

In one embodiment, the present invention provides methods to diagnose and/or predict susceptibility to Crohn's Disease by detecting the presence or absence of risk variants at the TLR5 locus and the presence or absence of Cbir1 and/or OmpC expression, where the presence of one or more risk variants at the TLR5 locus and the presence of Cbir1 and/or OmpC expression is indicative of susceptibility to Crohn's Disease. In another embodiment, the present invention provides methods of treatment of Crohn's Disease by detecting the presence of risk variants at the TLR5 locus and/or the presence of Cbir1 and/or OmpC, and treating the Crohn's Disease. In another embodiment, the risk variants at the TLR5 locus include F616L F allele and/or N592S S allele, where F616L F allele and N592S S allele are associated with OmpC expression. In another embodiment, the risk variants at the TLR5 locus include N592S N allele, where N592S S allele is associated with Cbir1 expression. In another embodiment, the individual is Jewish. In another embodiment, the N592S N allele is associated with a severe form of Crohn's Disease.

In one embodiment, the present invention provides methods of treatment of Inflammatory Bowel Disease through inhibition of TLR5 signaling.

III. Anti-Flagellin (Cbir1) Phenotypic and Genetic Crohn's Disease Associations As disclosed herein, the inventors examined the association between anti-CBir1 and clinical phenotypes and NOD2 variants in a large cohort of adult CD patients. Sera and genomic DNA were collected from 731 patients with CD and tested for immune responses to I2 (anti-I2), CBir1 (anti-CBir1), oligomannan (ASCA), and outer membrane porin C (anti-OmpC) and the 3 most common CD-associated NOD2 variants. Associations between anti-CBir1 and clinical phenotypes as well as NOD2 variants were evaluated.

As further disclosed herein, anti-CBir1 serum reactivity was significantly associated with fibrostenosis (FS), internal (IP), but not perianal (PP), penetrating disease phenotypes as well as small bowel (SB) involvement and SB surgery but negatively associated with UC-like CD. Multivariate logistic regression analysis showed that anti-CBir1 reactivity was independently associated with FS and UC-like CD irrespective of the antibody reactivity to I2, oligomannan or OmpC. However, anti-CBir1 was not independently associated with SB involvement or SB surgery. Assessing the contribution of CBir1 Ab reactivity to CD phenotypes, compared to the other 3 antibodies, showed that the magnitude of anti-CBir1 reactivity enhances the discrimination of FS, IP, UC-like CD and SB involvement, but not, SB surgery. Finally, although the frequency of anti-CBir1 was similar in patients with none vs. at least one NOD2 variant, the quantitative response to CBir1 flagellin was significantly higher in patients with CD carrying at least one NOD2 variant versus those carrying no variants (median anti-CBir1 titer 33.39 vs. 28.36, respectively; p=0.01).

As further disclosed herein, anti-CBir1 serum reactivity in CD patients is independently associated with FS and complicated SB CD. Quantitative, but not qualitative, response to CBir1 is also significantly associated with the CD-associated NOD2 variants.

In one embodiment, the present invention provides methods to diagnose and/or predict susceptibility to FS and/or complicated SB CD by determining the presence or absence of anti-Cbir1 reactivity. In another embodiment, the present invention provides methods of prognosis of FS and/or complicated SB CD by determining the presence or absence of anti-Cbir1 reactivity. In another embodiment, the present invention provides methods of treatment of FS and/or complicated SB CD by determining the presence or absence of anti-Cbir1 reactivity.

In one embodiment, the present invention provides methods to diagnose and/or predict susceptibility to Crohn's Disease by determining the presence or absence of a quantitative response to Cbir1 associated with the presence or absence of NOD2 variants. In another embodiment, the present invention provides methods of prognosis of Crohn's Disease by determining the presence or absence of a quantitative response to Cbir1 associated with the presence or absence of NOD2 variants. In another embodiment, the present invention provides methods of treatment of Crohn's Disease by determining the presence or absence of a quantititative response to Cbir1 associated with the presence or absence of NOD2 variants.

IV. Enhanced Cbir1 Specific Induction of Monocyte (1-1Beta and IL-6) and T Cell (Proliferation and IFN-gamma) Responses in Crohn's Disease Patients As disclosed herein, the inventors determined the effect of Cbir1 on innate and adaptive immune responses in Crohn's Disease patients. The inventors found Cbir1 enhanced IL-6 production of peripheral blood monocytes in CD patients, but not in UC or healthy donors. The inventors also found an inverse correlation in IL-6 production and anti-Cbir1 level. As further disclosed herein, the inventors showed Cbir1 peripheral blood T cell proliferation was higher in CD compared to UC or healthy donors. The inventors also determined that there is an increased amount of Cbir1 specific IFN-gamma-producing cells from involved CD colon compared to UC and control.

As further disclosed herein, Cbir1 induces enhanced innate and specific peripheral and mucosal T cell responses in Crohn's Disease patients. As further disclosed herein, the inventors show Cbir1 immune activation plays a role in the mucosal inflammation in CD.

In one embodiment, the present invention provides a method to diagnose Crohn's Disease in an individual by determining the presence or absence of Cbir1 enhanced IL-6 production, where the presence of Cbir1 enhanced IL-6 production is indicative of Crohn's Disease. In another embodiment, the present invention provides a method of treatment of Crohn's Disease by determining the presence or absence of Cbir1 enhanced IL-6 production, and treating the Crohn's Disease.

In one embodiment, the present invention provides a method of treating Crohn's Disease by determining the presence of a high magnitude of IL-6 production, and administering a therapeutically effective amount of anti-Cbir1.

In one embodiment, the present invention provides a method of diagnosing Crohn's Disease in an individual by determining the presence or absence of Cbir1-specific peripheral blood T cell proliferation, where the presence of Cbir1-specific peripheral blood T cell proliferation is indicative of Crohn's Disease.

In one embodiment, the present invention provides a method of diagnosing Crohn's Disease in an individual by determining the presence or absence of Cbir1-specific IFN-gamma producing cells, where the presence of Cbir1-specific IFN-gamma producing cells is indicative of Crohn's Disease. In another embodiment, the present invention provides methods of treatment of Crohn's Disease by determining the presence or absence of an increased amount of Cbir1-specific IFN-gamma producing cells, and treating the Crohn's Disease. Another method of treatment might also include modulation of Cbir1, anti-Cbir1 antibodies, IL-6, IFN-gamma producing cells, and/or peripheral blood T cells.

In one embodiment, the present invention provides methods of treatment of Crohn's Disease through inhibition of Cbir1-specific IFN-gamma signaling. In another embodiment, the present invention provides methods of treatment of Crohn's Disease through inhibition of IFN-gamma signaling.

Variety of Methods and Materials

A variety of methods can be used to determine the presence or absence of a variant allele or haplotype. As an example, enzymatic amplification of nucleic acid from an individual may be used to obtain nucleic acid for subsequent analysis. The presence or absence of a variant allele or haplotype may also be determined directly from the individual's nucleic acid without enzymatic amplification.

Analysis of the nucleic acid from an individual, whether amplified or not, may be performed using any of various techniques. Useful techniques include, without limitation, polymerase chain reaction based analysis, sequence analysis and electrophoretic analysis. As used herein, the term "nucleic acid" means a polynucleotide such as a single or double-stranded DNA or RNA molecule including, for example, genomic DNA, cDNA and mRNA. The term nucleic acid encompasses nucleic acid molecules of both natural and synthetic origin as well as molecules of linear, circular or branched configuration representing either the sense or antisense strand, or both, of a native nucleic acid molecule.

The presence or absence of a variant allele or haplotype may involve amplification of an individual's nucleic acid by the polymerase chain reaction. Use of the polymerase chain reaction for the amplification of nucleic acids is well known in the art (see, for example, Mullis et al. (Eds.), The Polymerase Chain Reaction, Birkhauser, Boston, (1994)).

A TaqmanB allelic discrimination assay available from Applied Biosystems may be useful for determining the presence or absence of a genetic variant allele. In a TaqmanB allelic discrimination assay, a specific, fluorescent, dye-labeled probe for each allele is constructed. The probes contain different fluorescent reporter dyes such as FAM and VICTM to differentiate the amplification of each allele. In addition, each probe has a quencher dye at one end which quenches fluorescence by fluorescence resonant energy transfer (FRET). During PCR, each probe anneals specifically to complementary sequences in the nucleic acid from the individual. The 5' nuclease activity of Taq polymerase is used to cleave only probe that hybridize to the allele. Cleavage separates the reporter dye from the quencher dye, resulting in increased fluorescence by the reporter dye. Thus, the fluorescence signal generated by PCR amplification indicates which alleles are present in the sample. Mismatches between a probe and allele reduce the efficiency of both probe hybridization and cleavage by Taq polymerase, resulting in little to no fluorescent signal. Improved specificity in allelic discrimination assays can be achieved by conjugating a DNA minor grove binder (MGB) group to a DNA probe as described, for example, in Kutyavin et al., "3'-minor groove binder-DNA probes increase sequence specificity at PCR extension temperature," Nucleic Acids Research 28:655-661 (2000)). Minor grove binders include, but are not limited to, compounds such as dihydrocyclopyrroloindole tripeptide (DPI,).

Sequence analysis may also be useful for determining the presence or absence of a variant allele or haplotype.

Restriction fragment length polymorphism (RFLP) analysis may also be useful for determining the presence or absence of a particular allele (Jarcho et al. in Dracopoli et al., Current Protocols in Human Genetics pages 2.7.1-2.7.5, John Wiley & Sons, New York; Innis et al., (Ed.), PCR Protocols, San Diego: Academic Press, Inc. (1990)). As used herein, restriction fragment length polymorphism analysis is any method for distinguishing genetic polymorphisms using a restriction enzyme, which is an endonuclease that catalyzes the degradation of nucleic acid and recognizes a specific base sequence, generally a palindrome or inverted repeat. One skilled in the art understands that the use of RFLP analysis depends upon an enzyme that can differentiate two alleles at a polymorphic site.

Allele-specific oligonucleotide hybridization may also be used to detect a disease-predisposing allele. Allele-specific oligonucleotide hybridization is based on the use of a labeled oligonucleotide probe having a sequence perfectly complementary, for example, to the sequence encompassing a disease-predisposing allele. Under appropriate conditions, the allele-specific probe hybridizes to a nucleic acid containing the disease-predisposing allele but does not hybridize to the one or more other alleles, which have one or more nucleotide mismatches as compared to the probe. If desired, a second allele-specific oligonucleotide probe that matches an alternate allele also can be used. Similarly, the technique of allele-specific oligonucleotide amplification can be used to selectively amplify, for example, a disease-predisposing allele by using an allele-specific oligonucleotide primer that is perfectly complementary to the nucleotide sequence of the disease-predisposing allele but which has one or more mismatches as compared to other alleles (Mullis et al., supra, (1994)). One skilled in the art understands that the one or more nucleotide mismatches that distinguish between the disease-predisposing allele and one or more other alleles are preferably located in the center of an allele-specific oligonucleotide primer to be used in allele-specific oligonucleotide hybridization. In contrast, an allele-specific oligonucleotide primer to be used in PCR amplification preferably contains the one or more nucleotide mismatches that distinguish between the disease-associated and other alleles at the 3' end of the primer.

A heteroduplex mobility assay (HMA) is another well known assay that may be used to detect a SNP or a haplotype. HMA is useful for detecting the presence of a polymorphic sequence since a DNA duplex carrying a mismatch has reduced mobility in a polyacrylamide gel compared to the mobility of a perfectly base-paired duplex (Delwart et al., Science 262:1257-1261 (1993); White et al., Genomics 12:301-306 (1992)).

The technique of single strand conformational, polymorphism (SSCP) also may be used to detect the presence or absence of a SNP and/or a haplotype (see Hayashi, K., Methods Applic. 1:34-38 (1991)). This technique can be used to detect mutations based on differences in the secondary structure of single-strand DNA that produce an altered electrophoretic mobility upon non-denaturing gel electrophoresis. Polymorphic fragments are detected by comparison of the electrophoretic pattern of the test fragment to corresponding standard fragments containing known alleles.

Denaturing gradient gel electrophoresis (DGGE) also may be used to detect a SNP and/or a haplotype. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (Sheffield et al., "Identifying DNA Polymorphisms by Denaturing Gradient Gel Electrophoresis" in Innis et al., supra, 1990).

Other molecular methods useful for determining the presence or absence of a SNP and/or a haplotype are known in the art and useful in the methods of the invention. Other well-known approaches for determining the presence or absence of a SNP and/or a haplotype include automated sequencing and RNAase mismatch techniques (Winter et al., Proc. Natl. Acad. Sci. 82:7575-7579 (1985)). Furthermore, one skilled in the art understands that, where the presence or absence of multiple alleles or haplotype(s) is to be determined, individual alleles can be detected by any combination of molecular methods. See, in general, Birren et al. (Eds.) Genome Analysis: A Laboratory Manual Volume 1 (Analyzing DNA) New York, Cold Spring Harbor Laboratory Press (1997). In addition, one skilled in the art understands that multiple alleles can be detected in individual reactions or in a single reaction (a "multiplex" assay). In view of the above, one skilled in the art realizes that the methods of the present invention for diagnosing or predicting susceptibility to or protection against CD in an individual may be practiced using one or any combination of the well known assays described above or another art-recognized genetic assay.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Genes Regulating the Expression of Antibody to CBIR1 Flagellin in Humans Are Located Within a Syntenic Region to the Major Mouse Colitogenic Locus Cdcs1

The inventors investigated the genetic determinants of Cbir1 response in human CD by linkage analysis of Cbir1 expression as a quantitative trait (QTL). The inventors measured Cbir1 serum levels in 968 individuals in 80 CD-only (no UC affected) and 57 Mixed (both CD and UC affected) families was performed by ELISA and a 10cM genome scan was performed with microsatellite markers. QTL analysis was performed using the SOLAR program.

The heritability of expression of serum antibodies to Cbir1 antigen in this study was 0.19 (p=0.0005). A peak multipoint LOD score for Cbir1 expression was observed for human chromosome 4 at 91 cM (LOD =1.82, marker ATA2A03). This LOD increased with bivariate linkage analysis of expression of both ASCA and Cbir1 antibodies (LOD=1.99). This region is syntenic to the mouse chromosome 3 Cdcs1 region containing the Nfkb1 gene.

This observation supports the role of genetic variation that determines response to Cbir1 flagellin in this region in both mouse and human and that genetic variation in the NF-kappa-B gene creates an abnormal innate response to enteric bacterial antigens that results in severe CD.

Example 2

TLR5 Polymorphisms are Associated with OmpC and CbiR1 Expression and with Severity of Crohn's Disease in Ashkenazi Jews The inventors investigated the association of TLR5 SNPs and serum expression of antibodies to microbial antigens in CD using a case/control design. In 889 CD patients and 236 controls, serum expression of OmpC and Cbir1 was measured by ELISA, and 3 TLR5 SNPs (R392X, N592S, F616L) were genotyped by TaqMan MGB. Chi-square was used to test for the association of allele with disease, clinical characteristics, and antibody combinations, and Wilcoxon and logistic regression for antibody expression levels and disease severity.

The F616L F allele was associated with the presence of OmpC expression in Jewish cases (the F allele was present in 93.3% of OmpC+, Jewish, CD cases and in 81.2% OmpC-, p=0.0025; p=0.0005 for trend through 3 genotypes). By multivariate analysis, the F/F genotype contributed to a higher level of OmpC expression in both ethnic groups (presence of F/F p=0.019; OR of F/F versus L/L, 2.02 95% CI 1.15-3.58). Similarly, the N592S S allele was associated with the presence of OmpC expression in Jewish cases (30.8% of OmpC+, Jewish, CD cases had the S allele compared with 19.5% OmpC-, p=0.02). In contrast, the N allele was associated with higher levels of Cbir1 flagellin expression (278 for N/N and N/S genotype and 190 for S/S, p=0.05 with logistic regression). On multivariate analysis, the N/N allele was associated with CD severity as defined by internal penetrating, perianal perforating and severe fibrostenosis combined (OR 6.88, 95% CI 1.65-28.6, p=0.0059).

TLR5 SNPs are associated with the level of OmpC expression, particularly in Jews. The observation that the opposite allele of one of the TLR5 SNPs is associated with Cbir1 flagellin, a TLR5 ligand, supports the concept that specific variation in genes of innate immune pathways govern variations between individuals in expression of specific antibodies to microbial antigens. The combination of these immune signals then leads to increasing severity of disease.

Example 3

Reduced Nuclear Factor (NF)-kB Expression in Cell Lines From Anti-Cbir1-Associated NFKB 1 Haplotypes The inventors determined whether the human NFKB1 gene is associated with anti-Cbir1 expression and tested the relationship between NFKB1 genetic variants and NF-kB expression. Single-nucleotide polymorphisms (SNPs) were selected to tag common Caucasian haplotypes and genotyped in 763 Crohn's disease (CD) and 254 controls using Illumina technology. Anti-Cbir1 antibody and *Saccharomyces cerevisiae* antibody (ASCA) were measured by ELISA. Nuclear proteins from Epstein-Barr virus (EBV)-transformed lymphoblastoid cell lines from subjects with specific haplotypes were extracted and electro mobility shift assay (EMSA) was performed. Quantitation of EMSA was performed by electric densitometry.

One NFKB1 haplotype, H3, was associated with ASCA expression (62% of ASCA positive patients had H3 compared with 51% of ASCA negative patients, p=0.023) and another, H1, was associated with anti-Cbir1 expression (64% of anti-Cbir1 positive subjects had H1 compared with 53% of anti-Cbir1 negative subjects, p=0.003). Using EBV-transformed cell lines from H3 positive H1 negative (n=11) and H1 positive H3 negative (n=14) subjects, the median NF-kB expression was lower fro patients with H1 compared with patients with H3 (median NF-kB expression for H3 was 1.79 compared with H1, 1.28, p=0.02, Wilcoxon test).

Human NFKB1 haplotypes were differentially associated with both ASCA and anti-Cbir1 expression. The anti-Cbir1-associated haplotype (H1) showed less NF-kB induction, even following EBV-signaling, normally a strong inducer. Differences due to H1 may be greater under less strong induction, eg. signals due to TLR in monocytes. These observations in humans are consistent with the reduced induction of NFKB1 driven inflammatory genes that is associated with the colitigenic Cdcs1 locus in the mouse.

Example 4

Reduced Nuclear Factor (NF)-kB Expression in Cell Lines From Anti-Cbir1-Associated NFKB1 Haplotypes: Subjects Recruitment of subjects at the Cedars-Sinai Medical Center Inflammatory Bowel Disease center was conducted under the approval of the Cedars-Sinai Medical Center Institutional Review Board. Disease phenotype was assigned using a combination of standard endoscopic, histological, and radiographic features. (a) The "family panel" consisted of 968 individuals total in 80 "CD-only" families with at least two members with Crohn's disease (CD) and no known members with ulcerative colitis (UC) and 57 "mixed" families with at least two members with either CD or UC. (b) The "case control panel" consisted of 763 CD patients, 351 UC patients and 254 controls, mainly spouses, matched on ethnicity (Ashkenazi Jewish and non-Jewish). There is no overlap between the family panel and the case control panel.

Example 5

Reduced Nuclear Factor (NF)-k8 Expression in Cell Lines From Anti-Cbir1-Associated NFKB1 Haplotypes: Genotyping DNA was isolated from Epstein Barr virus transformed lymphoblastoid cell lines using proteinase K digestion, organic extraction, and ethanol precipitation. (a) Whole Genome Linkage Study. 381 autosomal microsatellite markers from Weber set 9, average spacing ~10 cM, were genotyped using dye-labeled PCR products and measurement of size by computer-aided electrophoresis. (b) NFKB1 Association Study. The NFKB1 insertion/deletion polymorphism was genotyped using microsatellite methods as in Part a and size measurement using capillary electrophoresis (ABI 3100, Applied Biosystems, Foster City, Calif.). Single nucleotide markers (SNPs) were genotyped using two methods: the oligonucleotide ligation assay, Illumina Golden Gate technology, following the manufacturer's protocol (Illumina, San Diego, Calif.), and the 5'-extension reaction, TaqMan MGB technology, following the manufacturer's protocol (Applied Biosystems, Bulletin #4322856). Consistency of SNP genotyping between the two methods was checked for each SNP by genotyping 100 samples with both methods. SNPs were selected to tag the major Caucasian haplotypes using the "Tagger" option in the program Haploview applied to data from the International HapMap Project.

Example 6

Reduced Nuclear Factor (NF)-kB Expression in Cell Lines From Anti-Cbir1-Associated NFKB1 Haplotypes: Statistical Analysis The serum level of anti-CBir1 was log transformed to enable analyses based on the normal distribution. Varance components linkage analysis as implemented in the SOLAR computer program was used to estimate the heritability of anti-CBir1 level as a quantitative trait and to test for linkage of the microsatellite markers. Haplotypes were assigned from individual SNP data using the computer program PHASE v2. Association of NFKB1 haplotypes was tested using chi-square and the significance of results was assessed by applying a permutation test to the data in order to correct for the multiple testing of haplotypes.

Example 7

Reduced Nuclear Factor (NF)-kB Expression in Cell Lines From Anti-Cbir1-Associated NFKB1 Haplotypes: Linkage of anti-CBir1 Expression to Human Chromosome 4

A whole genome linkage study was conducted by analyzing 381 autosomal microsatellite markers against the serum level of anti-flagellin antibody (anti-CBir1) as a quantitative trait using variance components methods as implemented in the SOLAR computer program. First, the heritability, or measurement of the total genetic contribution to the trait of anti-CBir1 level, was estimated using this computer program to be 0.19 (p=0.0005). Second, based on the significance of this result, linkage of anti-CBir1 level across the human genome was calculated and three regions with LOD score greater than 1 were observed on chromosomes 4, 11, and 13. The highest LOD score was 1.82 and observed at position 91 cM on chromosome 4. When both the level of anti-CBir1 and anti-*Saccharomyces cerevisiae* antibody (ASCA) were used in a bivariate analysis of linkage in this region, the LOD score increased to 2.00.

The relationship between the mouse Cdcs1 locus and the human chromosome 4 linkage peak was next examined because: (a) genetic mapping had narrowed the Cdcs1 locus to a 7.6 Mb region on mouse chromosome 3 and that spans the mouse Nfkb1 gene, (b) the Cdcs1 phenotype included altered response to flagellin antigen, a phenotype related to the anti-CBir1 expression studied here, and (c) the human chromosome 4 linkage peak contained regions syntenic to the mouse chromosome 3. Using BLAT and the UCSC Genome Browser, the mouse region was located between human markers MFD324 and AFM248ZG9 (~105-113 cM) and so within 11 cM of the chromosome 4 linkage peak. These considerations led to the hypothesis that the human NFKB1 gene is associated with the serum expression of anti-CBir1 flagellin in IBD patients.

Example 8

Anti-Flagellin (Cbir1) Phenotypic and Genetic Crohn's Disease Associations

The inventors examined the association between anti-CBir1 and clinical phenotypes and NOD2 variants in a large cohort of adult CD patients. Sera and genomic DNA were collected from 731 patients with CD and tested for immune responses to I2 (anti-I2), CBir1 (anti-CBir1), oligomannan (ASCA), and outer membrane porin C (anti-OmpC) and the 3 most common CD-associated NOD2 variants. Associations between anti-CBir1 and clinical phenotypes as well as NOD2 variants were evaluated.

Anti-CBir1 serum reactivity was significantly associated with fibrostenosis (FS), internal (IP), but not perianal (PP), penetrating disease phenotypes as well as small bowel (SB) involvement and SB surgery but negatively associated with UC-like CD. Multivariate logistic regression analysis showed that anti-CBir1 reactivity was independently associated with FS and UC-like CD irrespective of the antibody reactivity to I2, oligomannan or OmpC. However, anti-CBir1 was not independently associated with SB involvement or SB surgery. Assessing the contribution of CBir1 Ab reactivity to CD phenotypes, compared to the other 3 antibodies, showed that the magnitude of anti-CBir1 reactivity enhances the discrimination of FS, IP, UC-like CD and SB involvement, but not, SB surgery. Finally, although the frequency of anti-CBir1 was similar in patients with none vs. at least one NOD2 variant, the quantitative response to CBir1 flagellin was significantly higher in patients with CD carrying at least one NOD2 variant versus those carrying no variants (median anti-CBir1 titer 33.39 vs. 28.36, respectively; p=0.01). Thus, anti-CBir1 serum reactivity in CD patients is independently associated with FS and complicated SB CD. Quantitative, but not qualitative, response to CBir1 is also significantly associated with the CD-associated NOD2 variants. The inventors demonstrate that the presence of anti-CBir1 is independently associated with complicated phenotypes, such as fibrostenosis, and negatively associated with UC like phenotype, but not the need for surgery in a large independent CD patient cohort. The addition of the magnitude of anti-CBir1 reactivity in CD patients to the antibody reactivity to multiple microbial antigens enhances the discrimination of CD phenotypes. The presence of anti-CBir1 is not directly associated with NOD2 variants and indicates other genetic alterations e.g. TLR5 variants associated with this antibody reactivity in patients with CD.

Example 9

Anti-Flagellin (Cbir1) Phenotypic and Genetic Crohn's Disease Associations: Patient Population A 731 combined CD patient cohort was ascertained from IBD patients assessed at the Cedars-Sinai Medical Center from 1988 to 2005. The first cohort included 303 patients which, has been previously characterized (8). The second cohort included 428 patients which were analyzed for the phenotypic association with anti-CBir1 reactivity. The association of NOD2 genotypes and anti-CBir1 reactivity was performed in the combined 731 patient cohort. All research-related activities were approved by the Cedars-Sinai Medical Center Institutional Review Board. The diagnosis of CD was based on standard endoscopic, histological, and radiographic features. At least 2 of the following characteristics were required for diagnosis: (1) clinical—perforating or fistulizing disease and obstructive symptoms secondary to stenosis or stricture; (2) endoscopic—deep linear or serpiginous ulcerations, discrete ulcers in normal-appearing mucosa, cobblestoning, and discontinuous or asymmetric inflammation; (3) radiographic—segmental disease (skip lesions), small bowel or colon strictures, stenosis, or fistula; or (4) histopathologic—submucosal or transmural inflammation, multiple granuloma, marked focal cryptitis, or focal chronic inflammatory infiltration within and between biopsies or skip lesions, including rectal sparing in the absence of local therapy.

Example 10

Anti-Flagellin (Cbir1) Phenotypic and Genetic Crohn's Disease Associations: Phenotype Designations CD patients were assigned phenotypes based on the standard previously published criteria (9-11). Those phenotypes include fibrostenosing, internal perforating, perianal fistulizing, and UC-like. Patients considered to have fibrostenotic disease had evidence of persistent small bowel obstruction or a history of resection for small bowel obstruction secondary to CD-related bowel stenosis. These patients had to have noninflammatory stenosis with evidence of partial or complete small bowel obstruction not due to adhesions on radiographic examination. Patients with a history of or evidence of small bowel perforation (abscesses) or fistula (enteroenteric, enterocutaneous, or enterovesicular fistulas) were considered to have internal perforating disease. Perianal perforating disease was defined as those patients with history of perianal abscess/fistula or rectovaginal fistula. Because it is recognized that CD behavior patterns are not mutually exclusive and can coexist within a given individual, a single patient may thus be represented with more than one phenotype designation. Most of the patients had phenotype designations performed at the time of consent for serological and genetic analysis. Some patients were enrolled at the time of surgery, but most were enrolled during the first consultation in the inflammatory bowel disease (IBD) clinic. However, the inventors' database is constantly being updated. In most cases, surgery occurred before enrollment or at the time of enrollment. If surgery occurred after enrollment, updates were made in the database. Disease location was based on endoscopic, histopathologic, and radiographic evidence of chronic inflammation and was defined as the presence of inflammation in the small bowel, colon, or both. Patients characterized as having small-bowel disease included those with only small-bowel disease and those with both small-bowel and colonic disease. Phenotype and disease location were assigned after discussion of the clinical data by IBD physicians who were blinded to the results of serological and genetic information. Significant small bowel surgeries included small bowel resections, ileocolonic resections, and stricturoplasties.

Example 11

Anti-Flagellin (Cbir1) Phenotypic and Genetic Crohn's Disease Associations: Anti-CBir1 ELISA Assay ELISA analysis of anti-CBir1 was performed as previously described (12) but using NH2-terminal fragment of CBir1 (147aa) without knowledge of diagnosis or other serology results. Briefly, ELISA plates were coated overnight with 100 ng/well of CBir1 then blocked with 1% BSA in PBS for 2 hours. Plates were washed and serum was added at a 1:200 dilution in 1% BSA-PBS and incubated for 30 minutes. After washing, horseradish-peroxidase conjugated anti-human IgG at a 1:10,000 dilution was added and incubated for 30 minutes. After another wash, the plates were incubated with tetramethylbenzidine substrate for 15 minutes. The reaction was stopped with 1 N sulfuric acid and read at 450 nm. Positive was defined as the mean+2 SD of the healthy controls. For Cohort 2 and the longitudinal cohorts and phenotype cohorts, this assay was modified to be more similar to the ANCA, OmpC and I2 protocols: alkaline phosphatase was substituted as the secondary conjugate and incubated for 1 hour followed by paranitrophenyl phosphate as substrate for 30 minutes.

Example 12

Anti-Flagellin (Cbir1) Phenotypic and Genetic Crohn's Disease Associations: Genotyping Three NOD2/CARD15 single-nucleotide polymorphisms (SNPs) have been previously associated with CD (4-5, 13): R675W (rs2066844; CEPH-IBD1-SNP8), G881R (rs2066845;CEPH-IBD1-SNP12), and 3020insC (rs2066847; CEPH-IBD1-SNP13) were adapted to the TaqMan MGB (Applied Biosystems, Foster City, Calif.) genotyping platform as previously described. TaqMan MGB is a 2-probe, 5'-exonuclease polymerase chain reaction assay that uses a 3-amino acid minor groove binder in the probes to give greater allele discrimination in the assay.

Example 13

Anti-Flagellin (Cbir1) Phenotypic and Genetic Crohn's Disease Associations: Serological Analysis All blood samples were taken at the time of consent and enrollment. Sera were analyzed for expression of pANCA, ASCA, anti-OmpC, and anti-I2 antibodies in a blinded fashion by enzyme-linked immunosorbent assay. Analysis of pANCA and immunoglobulin (Ig)G and IgA ASCA were performed at Cedars-Sinai Medical Center or Prometheus Laboratories (San Diego, Calif.) using the same technology. All assays for anti-OmpC and anti-I2 were performed at Cedars-Sinai. Antibody levels were determined and results expressed as enzyme-linked immunosorbent assay units (EU/mL), which are relative to a Cedars-Sinai laboratory (IgA-I2 and IgA-OmpC) or a Prometheus Laboratory standard (ANCA and IgA and IgG ASCA) that is derived from a pool of patient sera with well-characterized disease found to have reactivity to this antigen.

Example 14

Anti-Flagellin (Cbir1) Phenotypic and Genetic Crohn's Disease Associations: Statistical Analysis To determine the associations between antibody responses toward microbial antigens, autoantigens, and NOD2 genotype status and disease phenotype characteristics, univariate analyses with 2 tests were performed by using SAS (version 8.02; SAS Institute, Inc., Cary, N.C.). Odds ratios (OR) and 95% confidence intervals (CI) were calculated to compare the odds of positive serum reactivity toward CBir1 in the group of patients with a certain disease characteristic (e.g., fibrostenosing CD) with these odds in the group of patients without such a characteristic. To evaluate the association between disease phenotype characteristics and the combination of the level of immune response toward I2, OmpC, oligomannan, and CBir1 the sums of quartile scores for anti-I2, anti-OmpC, ASCA and CBir1 were calculated. For each antigen, patients whose antibody levels were in the 1st, 2nd, 3rd, and 4th quartile of the distribution were assigned a quartile score of 1, 2, 3, and 4, respectively. By adding individual quartile scores for each microbial antigen, a quartile sum score (range, 4-16) was obtained to represent the cumulative quantitative immune response toward all 4 antigens for each patient. Multivariate analysis with logistic regression modeling was also performed to determine the primary associations among qualitative serological responses with disease phenotypes.

Example 15

Anti-Flagellin (Cbir1) Phenotypic and Genetic Crohn's Disease Associations: Clinical, Serological and Genetic Characteristics of the Study Population The clinical, serologic and genetic characteristics of the CD patient cohort are shown in Table 1. The frequency of anti-CBir1 serum reactivity in the 428 independent CD patient cohort was 56%, which was similar to ~50% of the CD patients that the inventors previously determined in a smaller CD patient cohort. ASCA, anti-OmpC, and anti-I2 were present in 50%, 37%, and 58% of the patients, respectively. The frequency of any of 3 NOD2 variants tested in the inventors' cohort was 32%, whereas 68% carried no NOD2 variants. The inventors have recently found that the frequency of anti-CBir1 antibodies is greater in patients with increased number of antibody reactivity to I2, OmpC, and oligomannan, yet anti-CBir1 relates independently to CD when controlled for anti-I2, anti-OmpC and ASCA. In addition, there is no relationship between the level of response to CBir1 and any one of the other four antibodies.

TABLE 1

Clinical, Serologic and Genetic Characteristics of the CD Patient Cohort

| Characteristics | CD Cohort |
|---|---|
| Disease Phenotype (%) | (n = 428) |
| Fibrostenosis | 44.6 |
| Internal perforating | 32 |
| Perianal perforating | 31 |
| Disease Location: Small Bowel | 81 |
| Small Bowel surgery | 46.4 |
| Serological profile (%) | |
| ASCA positive | 50 |
| Anti-I2 positive | 58 |
| Anti-OmpC positive | 37 |
| Anti-CBir1 positive | 56 |
| NOD2 genotype for SNP 8, 12, and 13 (%) | (n = 731) |
| No mutations | 68.3 |
| Heterozygous | 26.5 |
| Compound heterozygous | 3.1 |
| Homozygous | 2.1 |

Example 16

Anti-Flagellin (Cbir1) Phenotypic and Genetic Crohn's Disease Associations: Antibody Response to CBir1 is Associated with Complicated Crohn's Disease Phenotypes The inventors have previously demonstrated an independent association between anti-CBir1 reactivity and complicated CD phenotypes e.g. internal perforating or fibrostenosis as well as SB involvement in the first 303 CD patient cohort. Given the independent association of antibody response to CBir1 and ASCA, anti-I2, and anti-OmpC, the inventors were interested in characterizing the phenotype of CD associated with the presence of anti-CBir1 in a second independent large cohort of CD patients. The inventors found that anti-CBir1 reactivity is significantly associated with SB and complicated CD phenotypes and is negatively associated with UC-like phenotype. The frequency of antibody response to CBir1 is higher in patients with fibrostenosis (FS) and internal penetrating (IP) CD phenotypes compared to those who lack these phenotypes. 69% of patients with fibrostenosis had reactivity against CBir1 compared to 50% of those who did not have this phenotype (p<0.0001). Similarly the percentage of CD patients with internal penetrating phenotype that were anti-CBir1+ were 68.5% whereas among CD patients without IP phenotype anti-CBir1-positivity was seen in 52% of patients (p=0.0015). There was an inverse relationship between anti-CBir1 reactivity and UC-like phenotype. Among CD patients with this phenotype 38.5% of them were anti-CBir1+ compared to 62% of patients who lack a UC-like phenotype (p<0.0001). The frequency of anti-CBir1 reactivity was also significantly associated with SB disease and SB surgery. Sixty percent of CD patients with SB involvement were anti-CBir1+ compared to 45% of patients who were free of SB disease (p=0.01). Similarly, the frequency of anti-CBir1 reactivity was higher among CD patients that have undergone surgery compared to those who haven't (64.5% vs. 51%, p=0.006).

The inventors further analyzed the association between disease phenotypes and anti-CBir1 reactivity stratified on the presence of Abs to 0, 1, 2 or all three other microbial antigens (oligomannan, I2, OmpC). As shown in Table 2, anti-CBir1 reactivity is significantly associated with FS, IP and complicated disease phenotypes, but not SB disease or SB surgery irrespective of Ab reactivity to other microbial antigens. Anti-CBir1 reactivity was also negatively associated with UC-like phenotype (Table 2).

TABLE 2

Association between Cbir1 and Crohn's disease phenotypes stratified on the presence of antibodies to 0, 1, 2, or all 3 other microbial antigens.

| Disease phenotype | Odds Ratio | P value |
| --- | --- | --- |
| Fibrostenosis | 1.9 (1.3-3.0) | 0.0024 |
| Internal penetrating | 1.6 (1-2.5) | 0.05 |
| Perianal penetrating | 1.4 (0.9-2.2) | 0.14 |
| UC-like | 0.4 (0.3-0.7) | 0.0007 |
| SB disease | 1.5 (0.9-2.5) | 0.1 |
| SB surgery | 1.4 (0.9-2.1) | 0.13 |
| Complicated | 2.1 (1.4-3.2) | 0.0004 |

Since antibody reactivity to ASCA, OmpC, and I2 has been previously associated with complicated CD phenotypes and NOD2 variants have been associated with small bowel involvement, young age of onset and strictruring disease, the inventors examined whether anti-CBir1 Ab reactivity is independently associated with complicated CD phenotype by performing logistic regression analysis. As shown in Table 3, anti-CBir1 reactivity is not independently associated with SB disease or SB surgery. Anti-CBir1 reactivity was independently associated with FS and complicated phenotypes and there was a trend for independent association with IP phenotypes (p=0.06, Table 3). There was a clear independent negative association between anti-CBir1 reactivity and UC-like phenotype (Table 3). In this patient cohort ASCA expression was the immune response with the strongest association between complicated disease phenotypes, SB involvement and surgery.

TABLE 3

Clinical Features: Results of Multivariate Logistic Regression

| | Small bowel disease (P) | Fibrostenosis (P) | Internal penetrating (P) | Small bowel surgery (P) | UC-like (P) | Complicated (P) |
| --- | --- | --- | --- | --- | --- | --- |
| Anti-CBir1 | 0.1 | 0.0033 | 0.06 | 0.15 | 0.001 | 0.0005 |
| Anti-OmpC | 0.62 | 0.5 | 0.07 | 0.16 | 0.8 | 0.1 |
| Anti-I2 | 0.53 | 0.01 | 0.08 | 0.04 | 0.99 | 0.01 |
| ASCA | <0.0001 | 0.003 | <0.0001 | <0.0001 | <0.0001 | <0.0001 |

Example 17

Anti-Flagellin (Cbir1) Phenotypic and Genetic Crohn's Disease Associations: Addition of anti-CBir1 Quantitative Immune Reactivity to ASCA, I2, and OmpC Enhances the Discrimination of Complicated CD Phenotypes The inventors analyzed the association between the magnitude of antibody reactivity to 3 CD-associated antibodies (ASCA, OmpC, I2) to disease phenotypes and compare it to the phenotype association when anti-CBir1 reactivity is added. The inventors found that the addition of anti-CBir1 antibody reactivity enhances the discrimination of complicated phenotypes, including FS and IP phenotypes. The proportion of patients with complicated disease phenotype e.g. FS or IP disease was higher in patients with the increasing reactivity to all 4 microbial antigens quantitatively. The inventors found no association between SB surgery and quantitative responses to all 4 antigens compared to 3 antigens alone, as assessed by quartile sum scores. There was also an enhanced discrimination of UC-like phenotype when quantitative responses between 3 vs. 4 antibodies were compared. The inventors' data indicate that the addition of the magnitude of anti-CBir1 reactivity to the other 3 CD associated Ab reactivity (oligomannan, I2, and OmpC) enhances the discrimination of complicated disease, SB involvement and UC-like phenotypes in patients with CD.

Example 18

Figure 1:
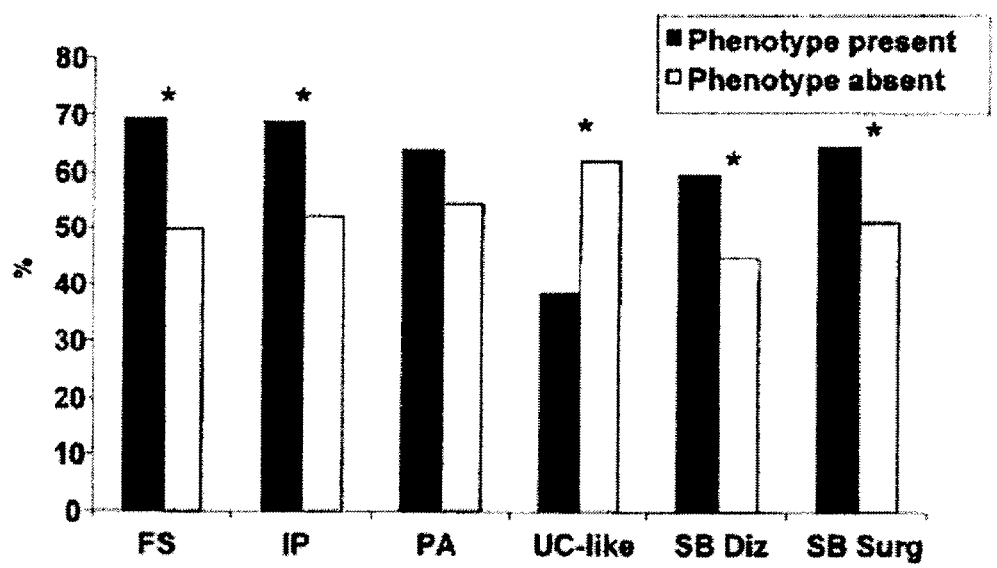
FIG. 1 depicts the frequency of anti-CBir 1 reactivity in CD patients with or without the indicative phenotype. FS=Fibrostenosis, IP=internal penetrating, PA=perianal penetrating, SB=small bowel, *p<0.05.
Figure 2:
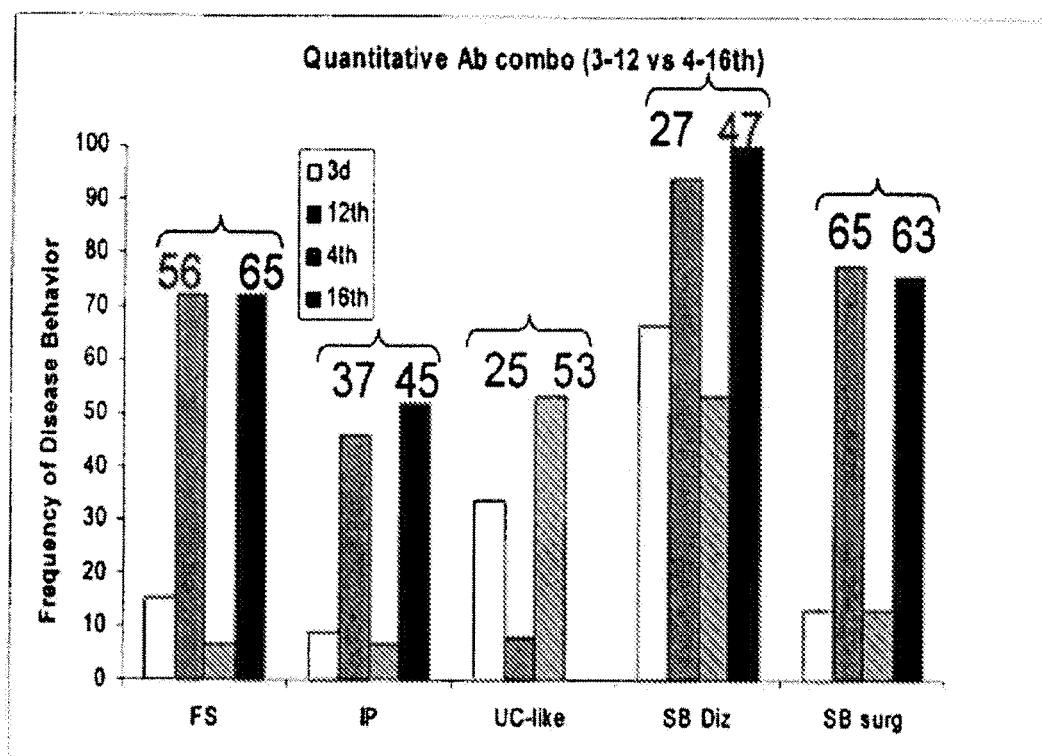
FIG. 2 depicts quantitative responses to 3 vs. 4 antigens enhances the discrimination of Fibrostenosis (FS), internal penetrating (IP), UC-like and small bowel (SB) disease but not SB surgery. The numbers represent the differences in the frequency of the indicated phenotype between the lowest vs. highest quartile sum scores for 3 (3d-12th) or 4 antibodies (4th-16th).
Figure 3:
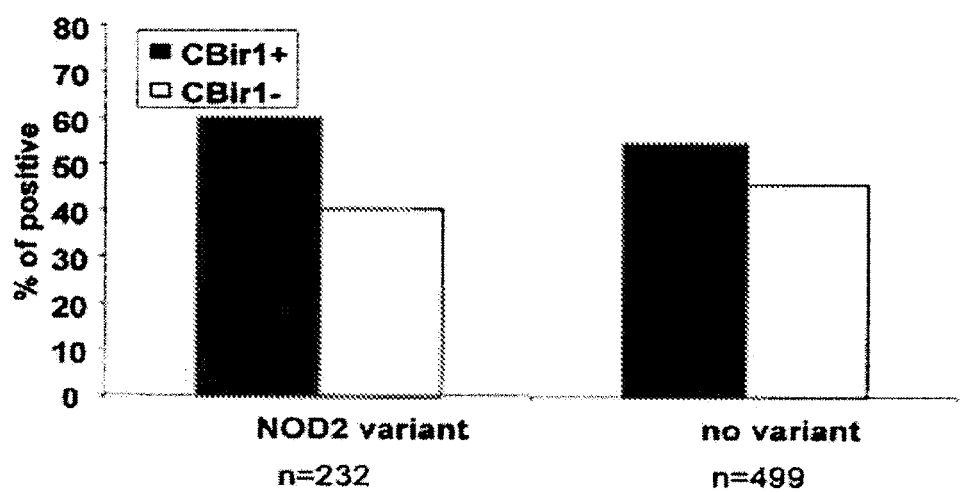
FIG. 3 depicts the level (lower panel) but not the presence (upper panel) of anti-CBir1 reactivity is associated with NOD2 variants in the combined CD cohort.
Figure 3:
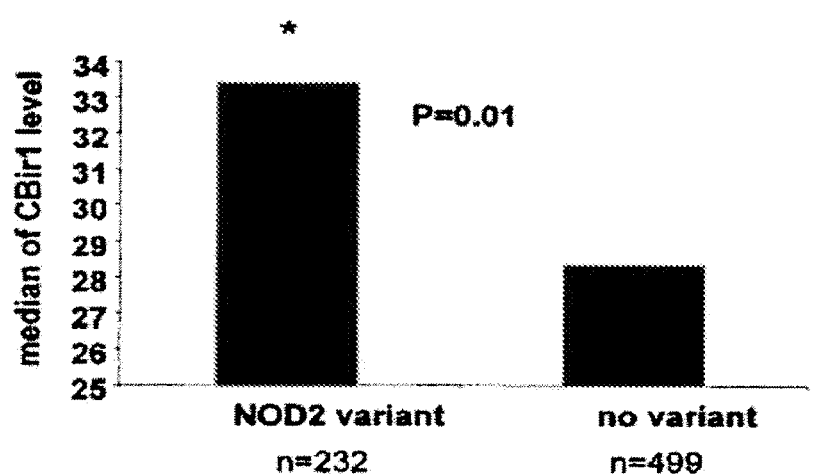
Figure 4A:
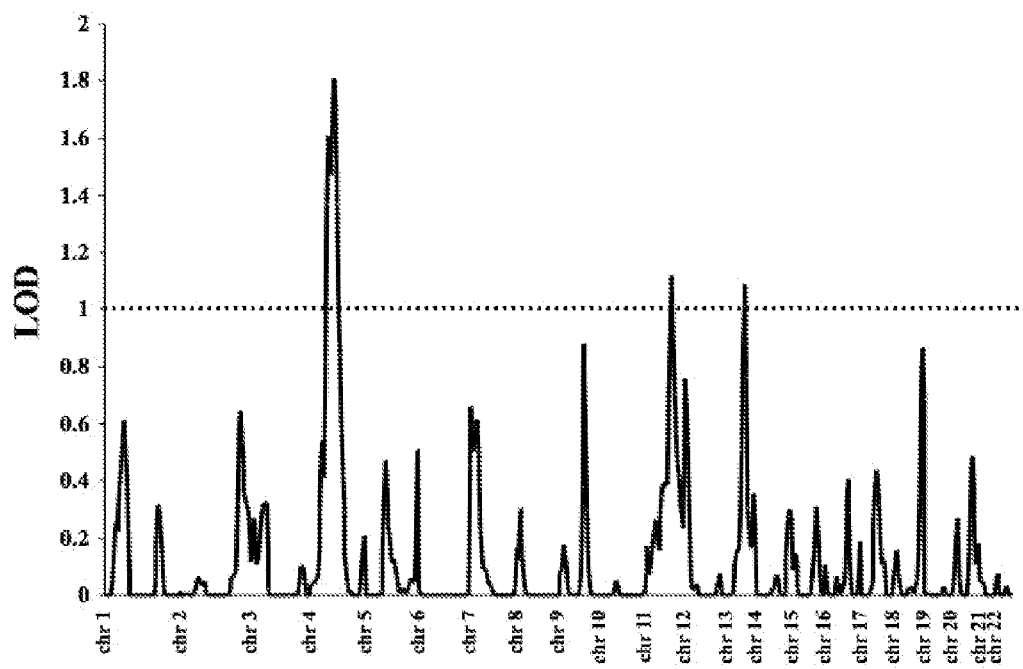
FIGS. 4A-B depict linkage of anti-CBir1 expression to human chromosome 4. Serum expression of anti-CBir1 and ASCA were treated as quantitative traits and LOD scores were calculated using the variance components method as implemented in the SOLAR computer program. Average spacing of microsatellite markers was ~10 cM. (a) Whole genome. LOD scores across the entire human genome are shown. (b) Chromosome 4. Detail for the highest LOD score on chromosome 4 (LOD=1.82 at 91 cM). The dotted line is for anti-CBir1 expression alone, and the solid line is for a bivariate analysis of anti-CBir1 and ASCA together. The position of the human region syntenic to the mouse sequence for the Cdcs1 locus is also shown.
Figure 4B:
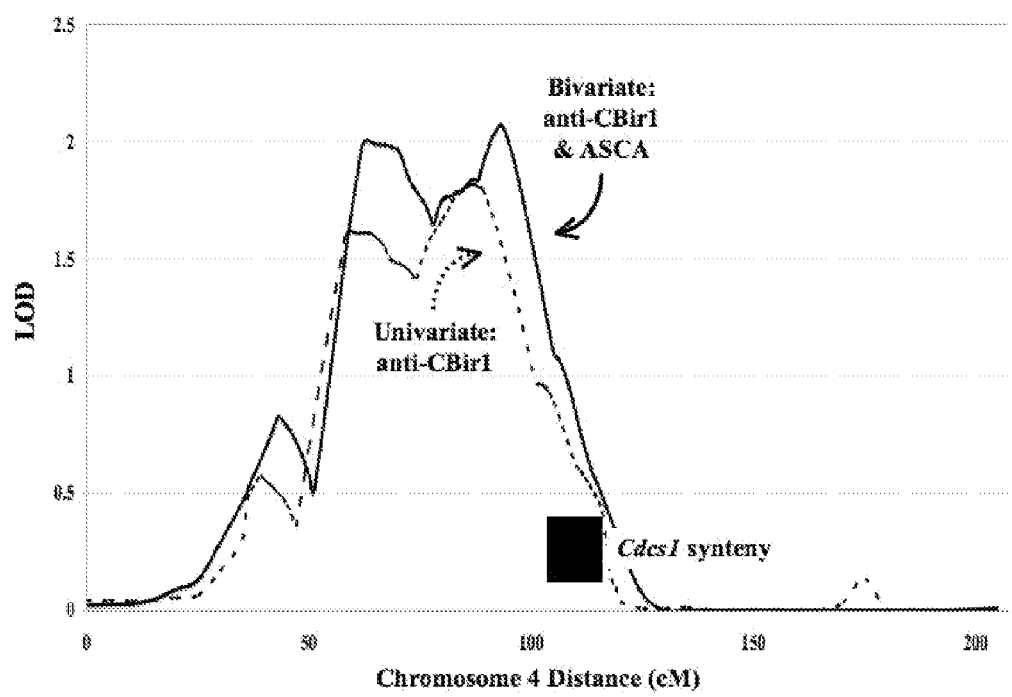

Anti-Flagellin (Cbir1) Phenotypic and Genetic Crohn's Disease Associations: Quantitative anti-CBir1 Reactivity is Associated with NOD2 Variants In the inventors' CD cohort, approximately 32% of patients were heterozygotes, compound heterozygotes or homozygotes for the 3 most common CD-associated NOD2 variants (R675W, G881 R, and 3020insC). To determine the association between CBir1 antibody reactivity and NOD2 variants, the inventors examined the frequency of CBir1 antibody reactivity among CD patients with none vs. any NOD2 variants present. The inventors observed no association between anti-CBir1 expression and the carriage of NOD2 variants. Among CD carriers of at least one NOD2 variant, 60% had anti-CBir1 reactivity and 40% lacked anti-CBir1 reactivity. Conversely, among patients with no NOD2 variants, anti-CBir1 was present in 55% of patients and absent in 45% (FIG. 3) (p=NS). However, when the inventors analyzed anti-CBir1 reactivity quantitatively the inventors found that NOD2 variants are significantly associated with the mean anti-CBir-1 Ab levels in patients with CD. The median serum Ab reactivity to CBir1 was 28.36 (range, 3.01-257) in patients with no NOD2 variants and 33.83 (range, 0-280) in patients with at least one NOD2 variant (FIG. 3, lower panel) (p=0.01).

Example 19

Enhanced Cbir1 Specific Induction of Monocyte (IL-1Beta and IL-6) and T Cell (Proliferation and IFN-gamma) Responses in Crohn's Disease Patients The inventors determined the effect of Cbir1 on innate and adaptive immune responses in Crohn's Disease patients. The inventors found the following: (1) Cbir1 enhanced IL-6 production of PB monocytes in CD patients, but not in UC or healthy donors; (2) an inverse correlation in IL-6 production and anti-Cbir1 level; (3) Cbir1-specific PB T cell proliferation was higher in CD compared to UC or healthy donors; (4) there is an increased amount of Cbir1 specific IFN-gamma-producing cells from involved CD colon compared to UC and control. The inventors showed that Cbir1 induces enhanced innate and specific peripheral and mucosal T cell responses in Crohn's Disease patients, and that Cbir1 immune activation plays a role in the mucosal inflammation in CD.

While the description above refers to particular embodiments of the present invention, it should be readily apparent to people of ordinary skill in the art that a number of modifications may be made without departing from the spirit thereof. The presently disclosed embodiments are, therefore, to be considered in all respects as illustrative and not restrictive. One skilled in the art will recognize many methods and materials similar or equivalent to those described herein, which could be used in the practice of the present invention. Indeed, the present invention is in no way limited to the methods and materials described. Furthermore, one of skill in the art would recognize that the invention can be applied to various inflammatory conditions and disorders and autoimmune diseases besides that of Crohn's Disease and/or Inflammatory Bowel Disease. It will also be readily apparent to one of skill in the art that the invention can be used in conjunction with a variety of phenotypes, such as serological markers, additional genetic variants, biochemical markers, abnormally expressed biological pathways, and variable clinical manifestations.

The invention claimed is:

1. A method of diagnosing susceptibility to Crohn's Disease in an individual, comprising:
   determining the presence or absence of one or more risk variants at the NFkB locus; and
   diagnosing susceptibility to Crohn's Disease based upon the presence of one or more risk variants at the NFkB locus.

2. The method of claim 1, wherein the individual is human.

3. The method of claim 2, wherein one of the one or more risk variants at the NFkB locus comprises ATA2A03.

4. The method of claim 1, wherein one of the one or more risk variants at the NFkB locus comprises SEQ. ID. NO.: 1.

5. The method of claim 1, wherein one of the one or more risk variants at the NFkB locus comprises H1 and/or H3 haplotypes at SEQ. ID. NO.: 2, SEQ. ID. NO.: 3, SEQ. ID, NO.: 4, SEQ. ID. NO.: 5, SEQ. ID. NO.: 6, SEQ. ID. NO.: 7, SEQ. ID. NO.: 8, SEQ. ID. NO.: 9, SEQ. ID. NO.: 10, SEQ. ID. NO.: 11, SEQ. ID. NO.: 12 and SEQ. ID. NO.: 13.

6. A method of diagnosing Crohn's Disease in an individual, comprising:
   determining the presence or absence of NFkB haplotype H3;
   determining the presence or absence of Anti-Cbir1 antibody and Saccharomyces cerevisiae antibody (ASCA) reactivity; and
   diagnosing Crohn's Disease based upon the presence of NFkB haplotype H3 and the presence of Anti-Cbir1 antibody and Saccharomyces cerevisiae antibody (ASCA) reactivity.

7. The method of claim 6, wherein the NFkB haplotype H3 comprises H3 alleles at positions SEQ. ID. NO.: 2, SEQ. ID. NO.: 3, SEQ. ID. NO.: 4, SEQ. ID. NO.: 5, SEQ. ID. NO.: 6, SEQ. ID. NO,: 7, SEQ. ID. NO.: 8, SEQ. ID. NO.: 9, SEQ. ID. NO.; 10, SEQ. ID. NO.: 11. SEQ. ID. NO.: 12 and SEQ. ID. NO.: 13.

8. A method of diagnosing Crohn's Disease in an individual, comprising:
   determining the presence or absence of NFkB haplotype H1;
   determining the presence or absence of Cbir1 reactivity; and
   diagnosing Crohn's Disease based upon the presence of NFkB haplotype H1 and the presence of Cbir1 reactivity.

9. The method of claim 8, wherein the NFkB haplotype H1 comprises H1 alleles at positions SEQ. ID. NO.: 2, SEQ. ID. NO.: 3, SEQ. ID. NO.: 4, SEQ. ID. NO.: 5, SEQ. ID. NO.: 6, SEQ. ID. NO.: 7, SEQ. ID. NO.: 8, SEQ. ID. NO.: 9, SEQ. ID. NO.: 10, SEQ. ID. NO.: 11, SEQ. ID. NO.: 12 and SEQ. ID. NO.: 13.

10. A method of treating Crohn's Disease in an individual, comprising:

determining the presence or absence of NFkB haplotype H3;

determining the presence or absence of ASCA reactivity; and treating the Crohn's Disease.

11. A method of treating Crohn's Disease in an individual, comprising:

determining the presence or absence of NFkB haplotype H1;

determining the presence or absence of Cbir1 reactivity; and treating the Crohn's Disease.

* * * * *

UNITED STATES PATENT AND TRADEMARK OFFICE
CERTIFICATE OF CORRECTION

PATENT NO. : 8,153,443 B2  
APPLICATION NO. : 12/599549  
DATED : April 10, 2012  
INVENTOR(S) : Kent D. Taylor et al.

Page 1 of 1

It is certified that error appears in the above-identified patent and that said Letters Patent is hereby corrected as shown below:

In the Specifications:

In column 1, line 13, please insert the following:

--FEDERAL SUPPORT  
The U.S. Government has a paid-up license in this invention and the right in limited circumstances to require the patent owner to license others on reasonable terms as provided for by the terms of Grant Nos. DK046763 and DC071176 awarded by the National Institutes of Health.--

In column 4, under the "Brief Description of Drawings" at lines 9-32, the description should read as follows:

FIGS. 5A-C depict NFKB1 SNPs and haplotypes. This cartoon showing the location of NFKB1 SNPs studied was created with the aid of the UCSC Genome Browser. (a) Diagram of the NFKB1 gene. The NFKB1 gene is located on chromosome 4 at the basepair location shown on Build 16 of the human genome project. Vertical lines show the position of exons. The position of the promoter insertion/deletion polymorphism is also shown. (b) List of SNPs studied. Accession numbers ("rs numbers") in the dbSNP of the National Center for Biotechnology Information are listed along with arrows showing their position along the NFKB1 gene. Polymorphisms genotyped in this study are listed with their positions along the gene. SNPs were selected using the Tagger option of the Haploview program applied to data for the Caucasian population from the International HapMap Project, with some redundancy in case of the failure of an individual SNP in the Illumina genotyping platform. (c) The most common NFKB1 haplotypes observed in this study. The SNP combinations that make up the six major haplotypes are shown, along with the frequency in the controls of this study are listed. "2" refers to the observed minor allele of each SNP in the controls.

Signed and Sealed this  
Fourth Day of December, 2012

David J. Kappos  
*Director of the United States Patent and Trademark Office*

UNITED STATES PATENT AND TRADEMARK OFFICE
CERTIFICATE OF CORRECTION

PATENT NO. : 8,153,443 B2  
APPLICATION NO. : 12/599549  
DATED : April 10, 2012  
INVENTOR(S) : Kent D. Taylor et al.

Page 1 of 1

It is certified that error appears in the above-identified patent and that said Letters Patent is hereby corrected as shown below:

In the Specifications:

In column 1, line 13, please insert the following:

--FEDERAL SUPPORT  
The U.S. Government has a paid-up license in this invention and the right in limited circumstances to require the patent owner to license others on reasonable terms as provided for by the terms of Grant Nos. DK046763 and DK071176 awarded by the National Institutes of Health.--

In column 4, under the "Brief Description of Drawings" at lines 9-32, the description should read as follows:

FIGS. 5A-C depict NFKB1 SNPs and haplotypes. This cartoon showing the location of NFKB1 SNPs studied was created with the aid of the UCSC Genome Browser. (a) Diagram of the NFKB1 gene. The NFKB1 gene is located on chromosome 4 at the basepair location shown on Build 16 of the human genome project. Vertical lines show the position of exons. The position of the promoter insertion/deletion polymorphism is also shown. (b) List of SNPs studied. Accession numbers ("rs numbers") in the dbSNP of the National Center for Biotechnology Information are listed along with arrows showing their position along the NFKB1 gene. Polymorphisms genotyped in this study are listed with their positions along the gene. SNPs were selected using the Tagger option of the Haploview program applied to data for the Caucasian population from the International HapMap Project, with some redundancy in case of the failure of an individual SNP in the Illumina genotyping platform. (c) The most common NFKB1 haplotypes observed in this study. The SNP combinations that make up the six major haplotypes are shown, along with the frequency in the controls of this study are listed. "2" refers to the observed minor allele of each SNP in the controls.

This certificate supersedes the Certificate of Correction issued December 4, 2012.

Signed and Sealed this  
Nineteenth Day of February, 2013

Teresa Stanek Rea  
*Acting Director of the United States Patent and Trademark Office*